US010493457B2

(12) United States Patent
Croquette et al.

(10) Patent No.: US 10,493,457 B2
(45) Date of Patent: Dec. 3, 2019

(54) SAMPLE STORAGE AND RETRIEVAL SYSTEM

(71) Applicant: BROOKS AUTOMATION, INC., Chelmsford, MA (US)

(72) Inventors: Etienne Croquette, Cheshire (GB); Rhett Affleck, Poway, CA (US); Robin Grimwood, Chelford (GB)

(73) Assignee: Brooks Automation, Inc., Chelmsford, MA (US)

( * ) Notice: Subject to any disclaimer, the term of this patent is extended or adjusted under 35 U.S.C. 154(b) by 0 days.

(21) Appl. No.: 14/671,423

(22) Filed: Mar. 27, 2015

(65) Prior Publication Data

US 2015/0273468 A1    Oct. 1, 2015

Related U.S. Application Data

(60) Provisional application No. 61/971,646, filed on Mar. 28, 2014.

(51) Int. Cl.
*B01L 3/00*    (2006.01)
*B01L 9/06*    (2006.01)
(Continued)

(52) U.S. Cl.
CPC ............ *B01L 3/50825* (2013.01); *B01L 9/06* (2013.01); *B01L 9/50* (2013.01); *B25J 15/0047* (2013.01); *B25J 15/0206* (2013.01); *B25J 15/0608* (2013.01); *B25J 19/02* (2013.01); *G01N 35/00009* (2013.01); *G01N 35/0099* (2013.01); *G01N 35/04* (2013.01); *B01L 2200/18* (2013.01); *B01L 2300/021* (2013.01); *B01L 2300/042* (2013.01); *B01L 2300/046* (2013.01); *B01L 2300/0609* (2013.01);
(Continued)

(58) Field of Classification Search
CPC ...... G01N 35/00; G01N 35/02; G01N 35/026; G01N 35/04; G01N 35/10; G01N 2035/00178; G01N 2035/0401; G01N 2035/0403; G01N 2035/0405; G01N 2035/0406; G01N 2035/041; B01L 3/50; B01L 3/502; B01L 3/5082; B01L 3/50825
USPC .................... 422/63, 65, 547, 560, 561, 562
See application file for complete search history.

(56) References Cited

U.S. PATENT DOCUMENTS

| 4,522,089 A | 6/1985 | Alvi |
| 5,452,932 A | 9/1995 | Griffin |

(Continued)

FOREIGN PATENT DOCUMENTS

| CH | 670794 | 7/1989 |
| EP | 2191942 | 6/2010 |

(Continued)

OTHER PUBLICATIONS

International Search Report, International Application No. PCT/US2015/023261, dated Oct. 19, 2015.

(Continued)

*Primary Examiner* — Jill A Warden
*Assistant Examiner* — Dwayne K Handy
(74) *Attorney, Agent, or Firm* — Colin C. Durham; Perman & Green, LLP

(57) ABSTRACT

A sample storage including a frame and an array of sample container holding areas disposed within the frame where a spacing between adjacent sample container holding areas is independent of a gripping area for sample containers held by the sample storage.

7 Claims, 30 Drawing Sheets

(51) Int. Cl.
  *B01L 9/00* (2006.01)
  *G01N 35/00* (2006.01)
  *G01N 35/04* (2006.01)
  *B25J 15/00* (2006.01)
  *B25J 15/02* (2006.01)
  *B25J 15/06* (2006.01)
  *B25J 19/02* (2006.01)

(52) U.S. Cl.
  CPC ............... *B01L 2300/1883* (2013.01); *G01N 2035/00425* (2013.01); *G01N 2035/00435* (2013.01); *G01N 2035/00445* (2013.01)

(56) References Cited

U.S. PATENT DOCUMENTS

| | | | |
|---|---|---|---|
| 6,017,496 | A | 1/2000 | Nova et al. |
| 6,216,340 | B1 | 4/2001 | Fassbind et al. |
| 6,298,684 | B1 | 10/2001 | Mitsuyoshi |
| 6,431,622 | B1 | 8/2002 | Depeursinge et al. |
| 2002/0132354 | A1 | 9/2002 | Downs et al. |
| 2003/0049170 | A1 | 3/2003 | Tamura et al. |
| 2003/0194353 | A1 | 10/2003 | Gilbert et al. |
| 2003/0209091 | A1 | 11/2003 | Fattinger et al. |
| 2006/0054572 | A1 | 3/2006 | Sygall et al. |
| 2008/0128970 | A1 | 6/2008 | Holden et al. |
| 2010/0129789 | A1 | 5/2010 | Self et al. |
| 2013/0136569 | A1 | 5/2013 | Rosmarin et al. |
| 2013/0151004 | A1 | 6/2013 | Winter et al. |
| 2014/0106386 | A1 | 4/2014 | Umeno et al. |

FOREIGN PATENT DOCUMENTS

| | | |
|---|---|---|
| JP | 0247570 | 3/1990 |
| JP | 0298667 | 4/1990 |
| JP | 2003535348 | 11/2003 |
| JP | 2004004070 | 1/2004 |
| JP | 2007278970 | 10/2007 |
| JP | 2013535691 | 9/2013 |
| WO | 0194016 | 12/2001 |
| WO | 2012018993 | 2/2012 |
| WO | 2013002268 | 1/2013 |
| WO | 2013068636 | 5/2013 |

OTHER PUBLICATIONS

Partial International Search Report, International Application No. PCT/US2015/023261, dated Jun. 24, 2015.

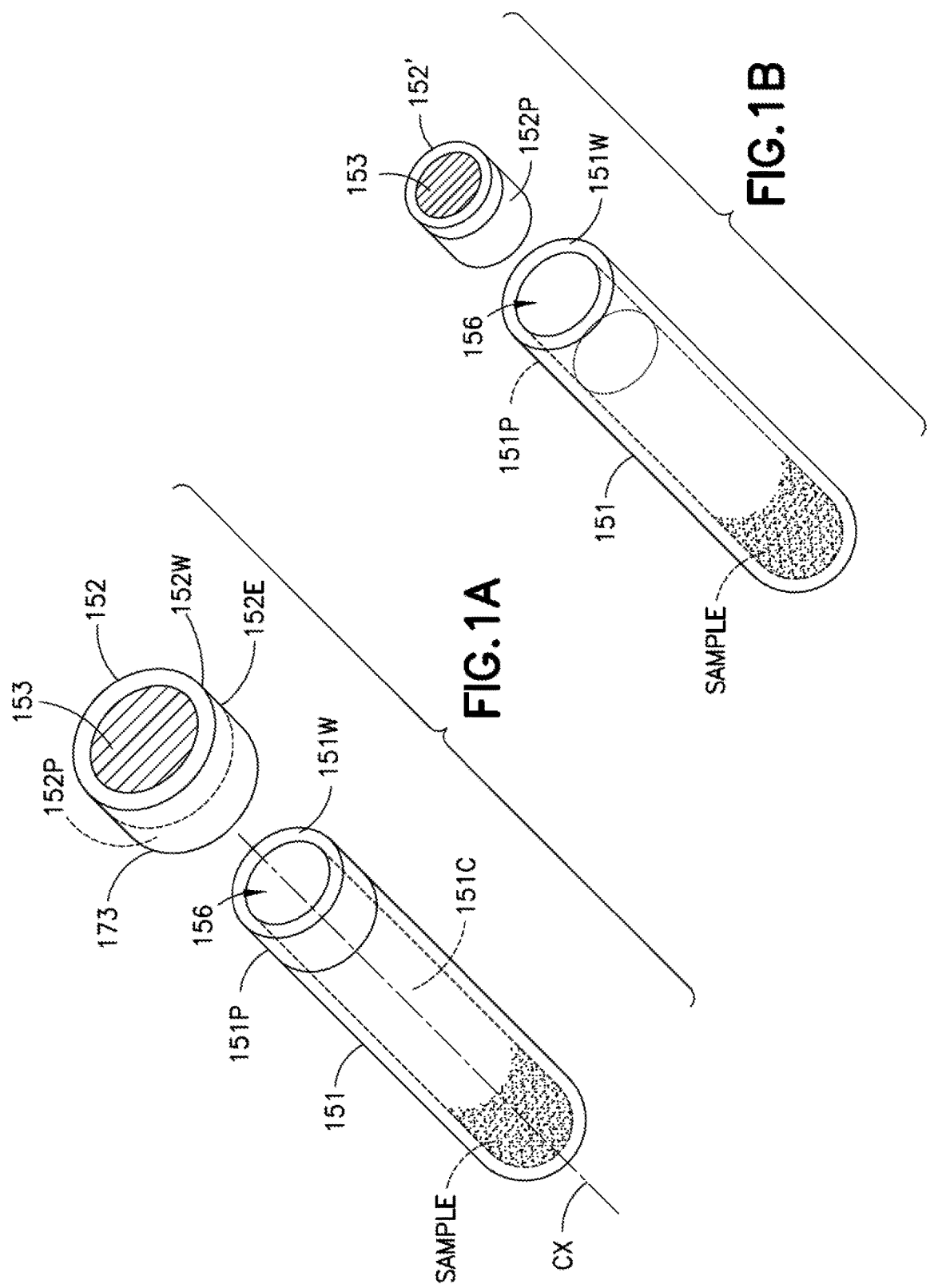

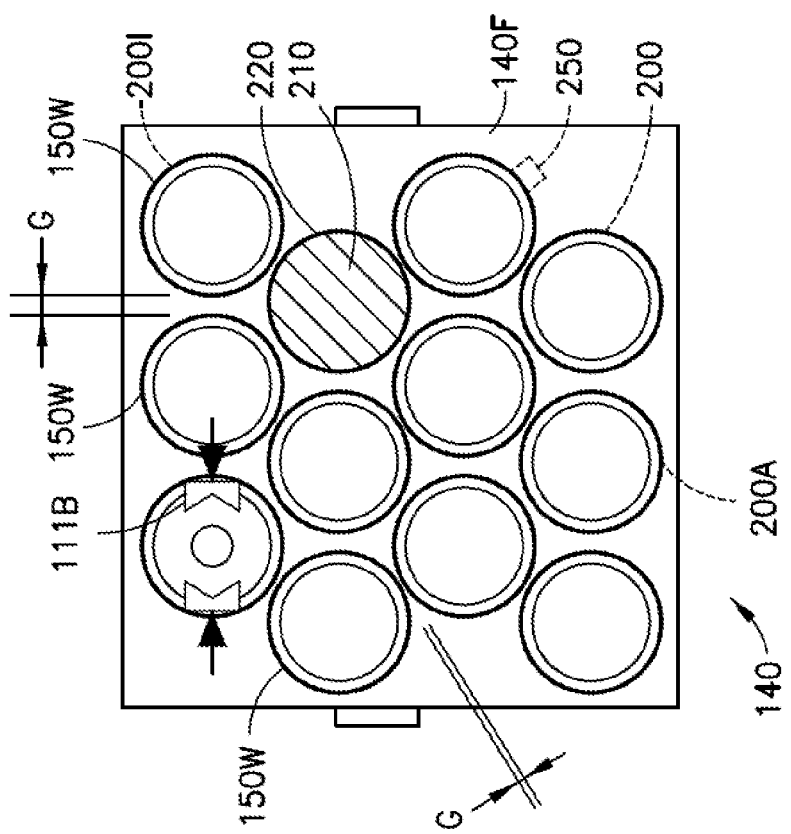
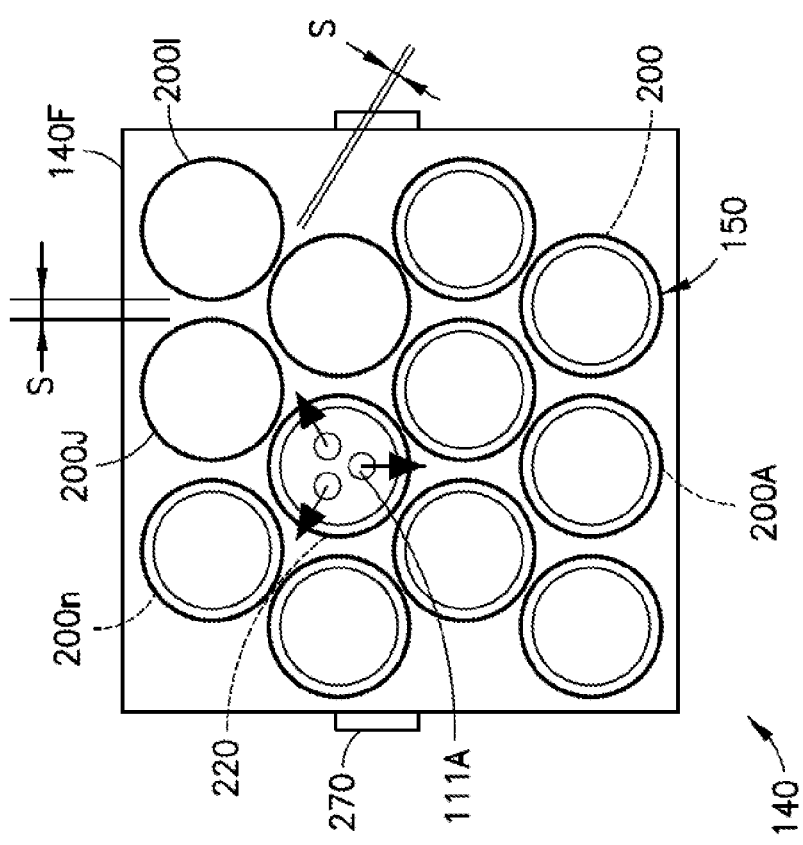
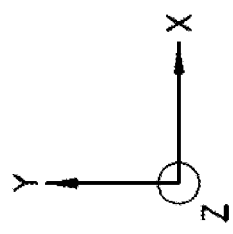
FIG.2B
FIG.2A

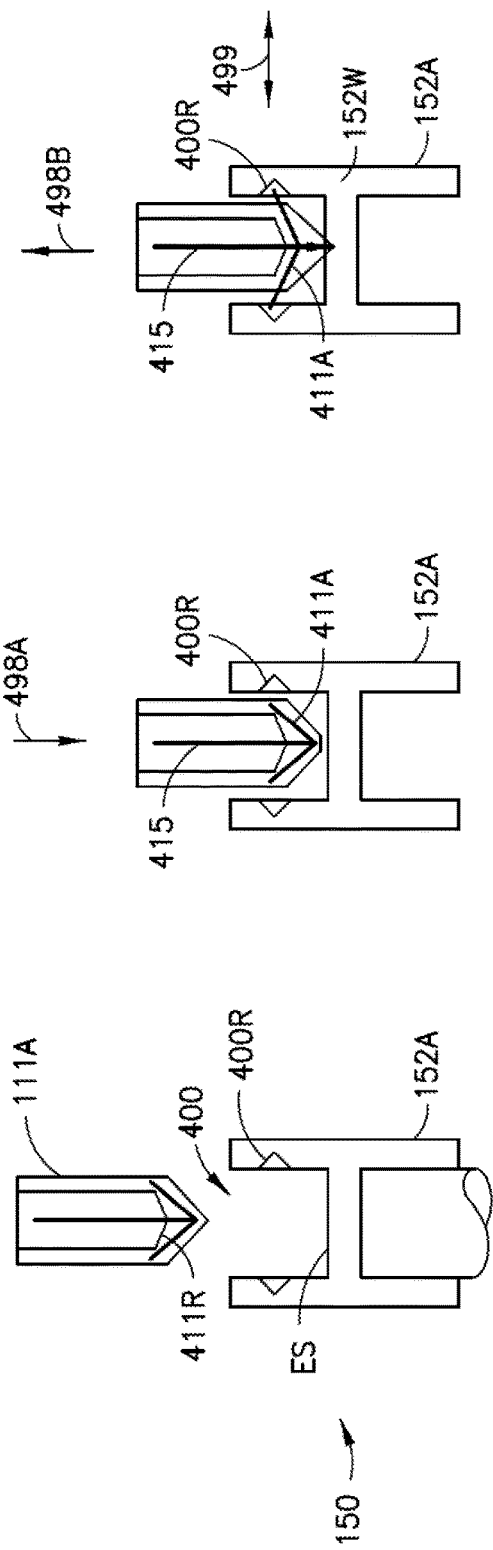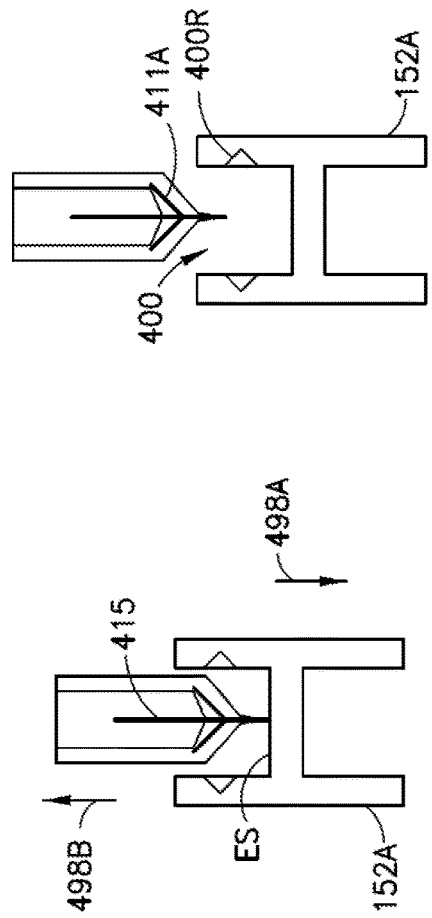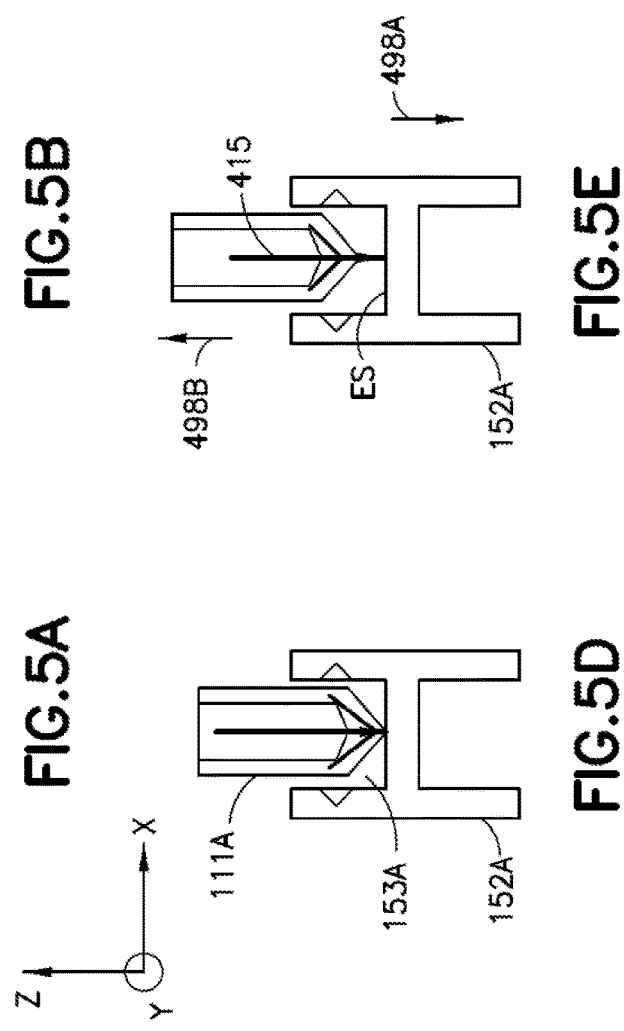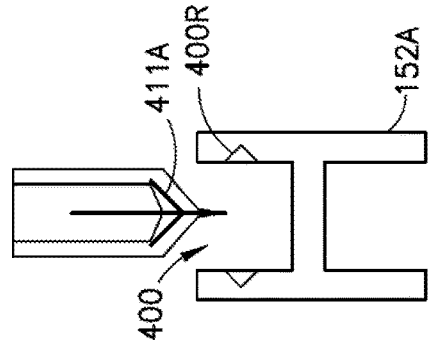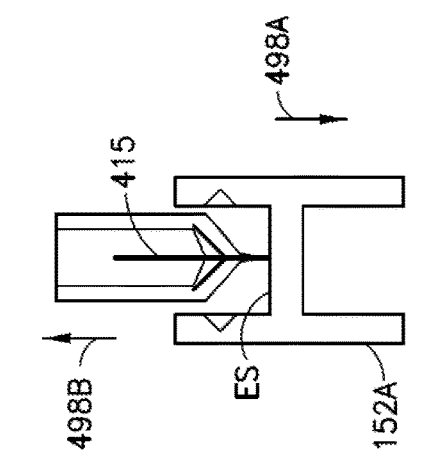

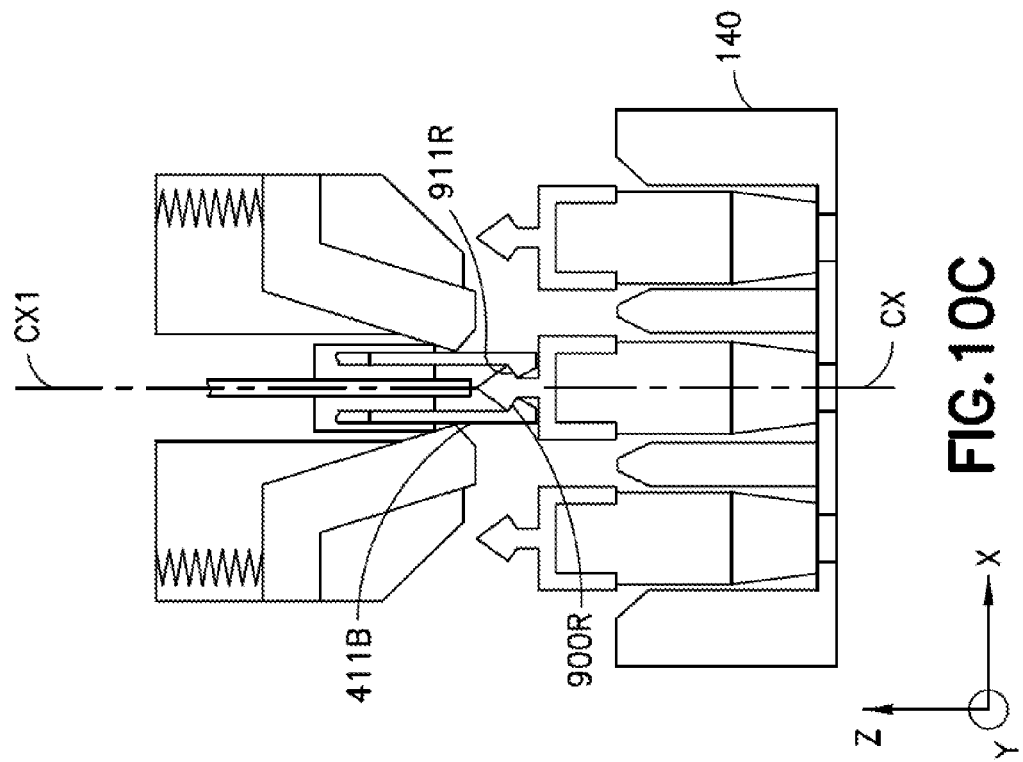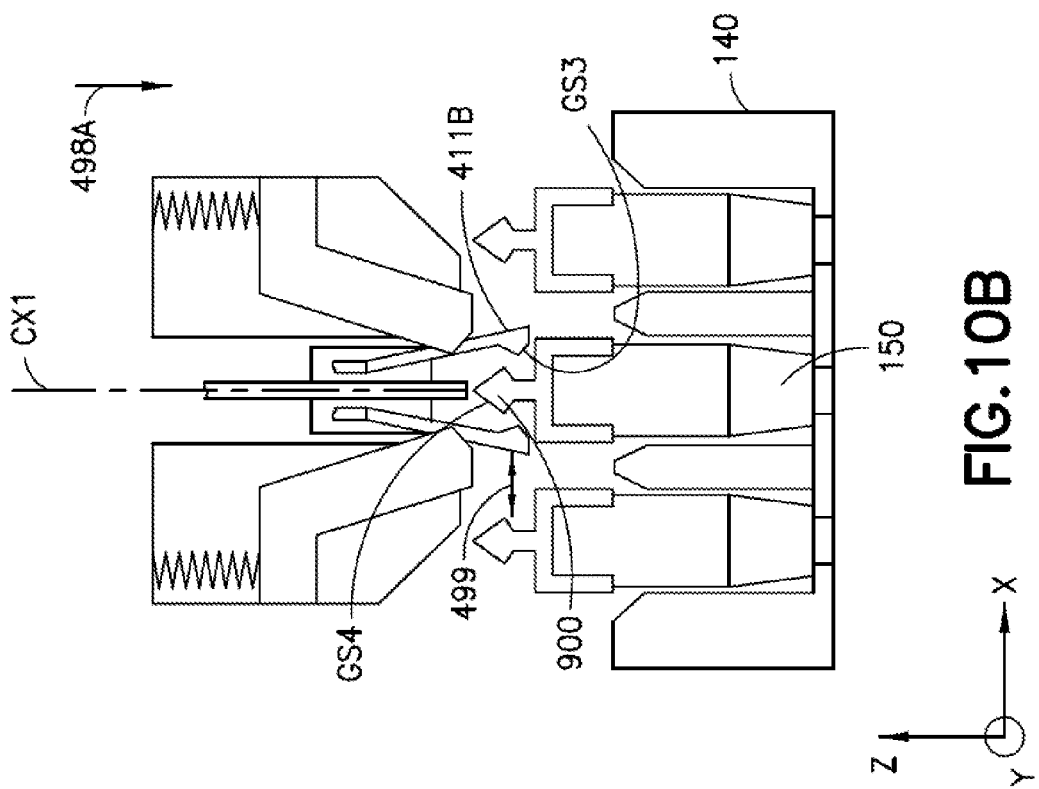

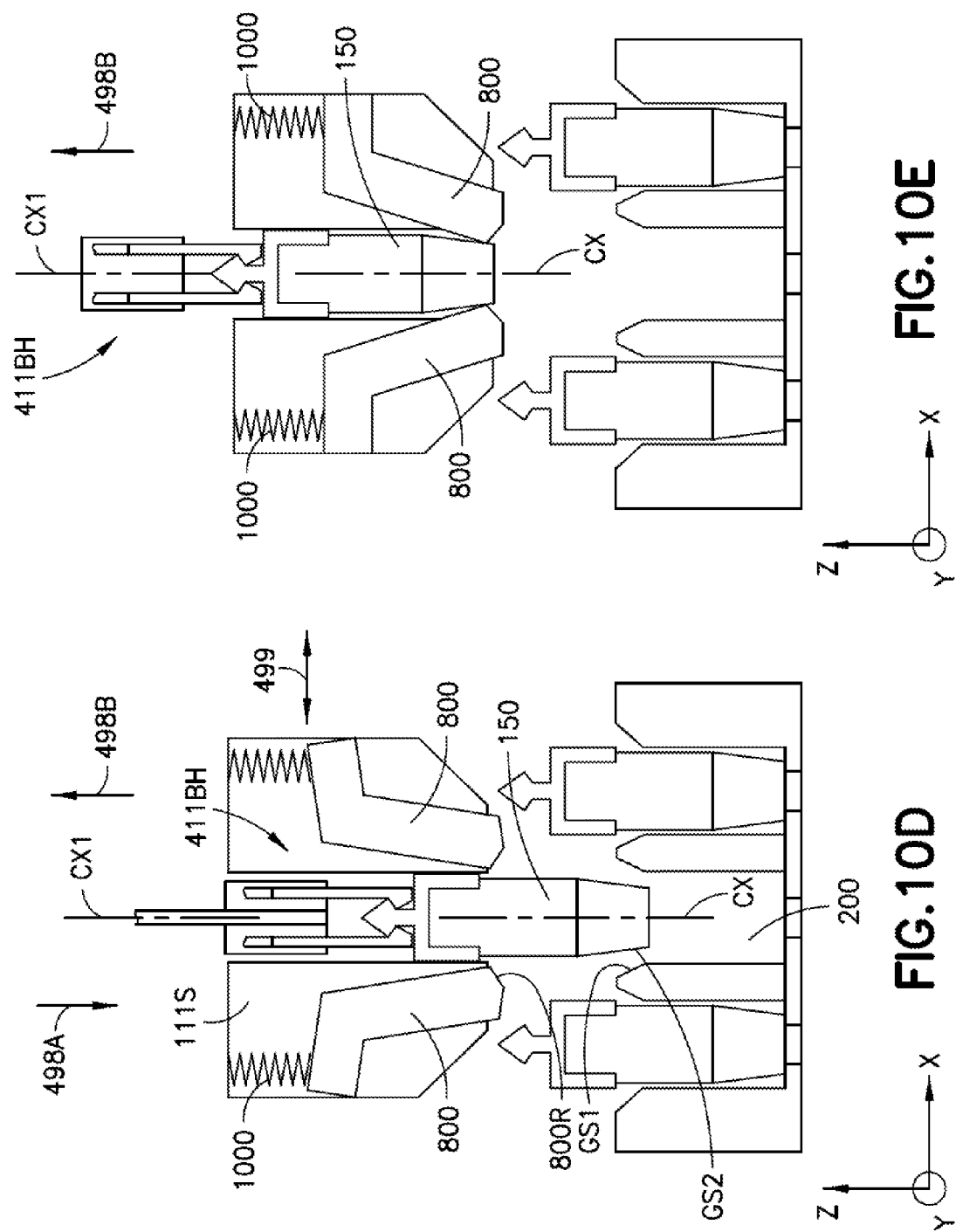

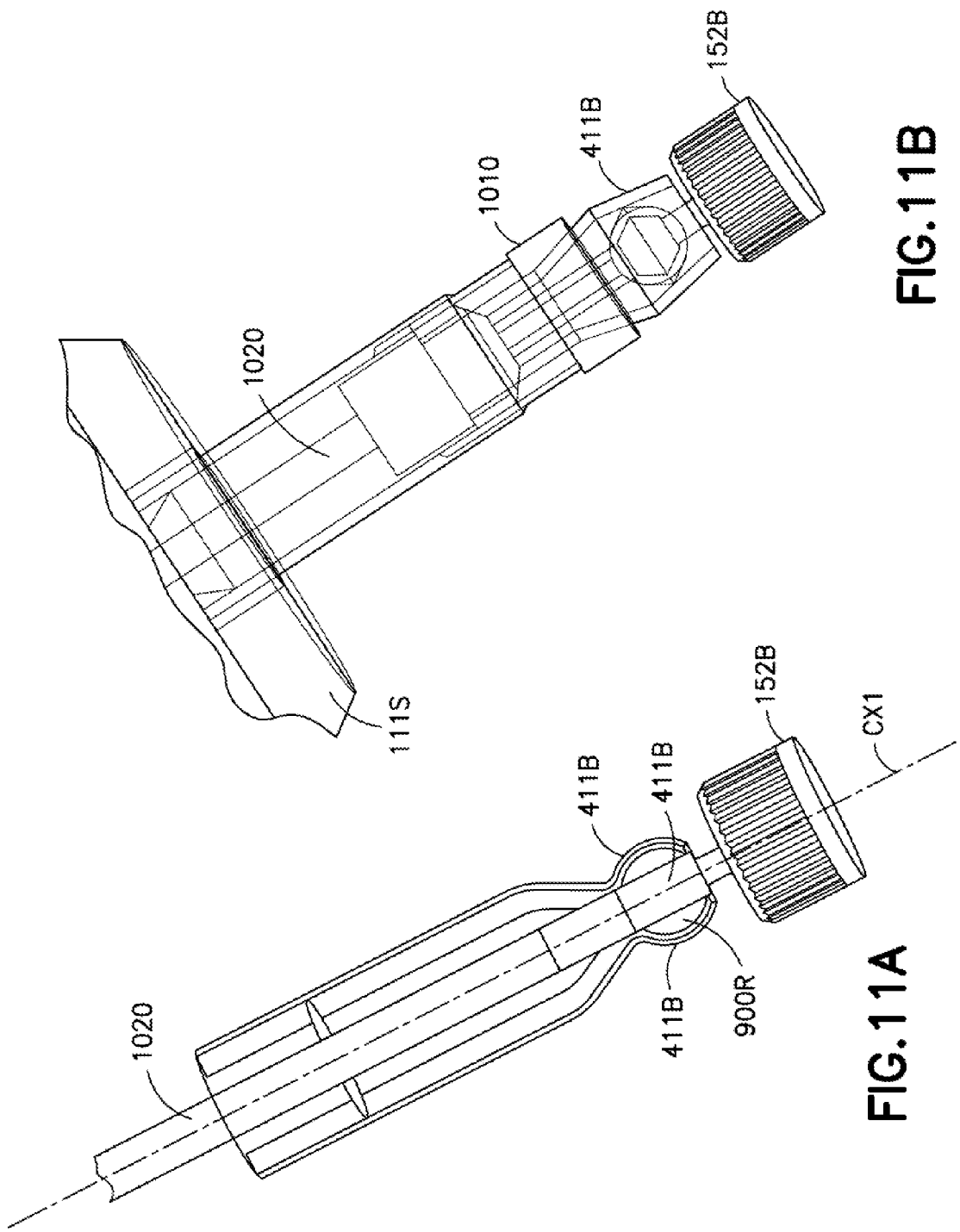

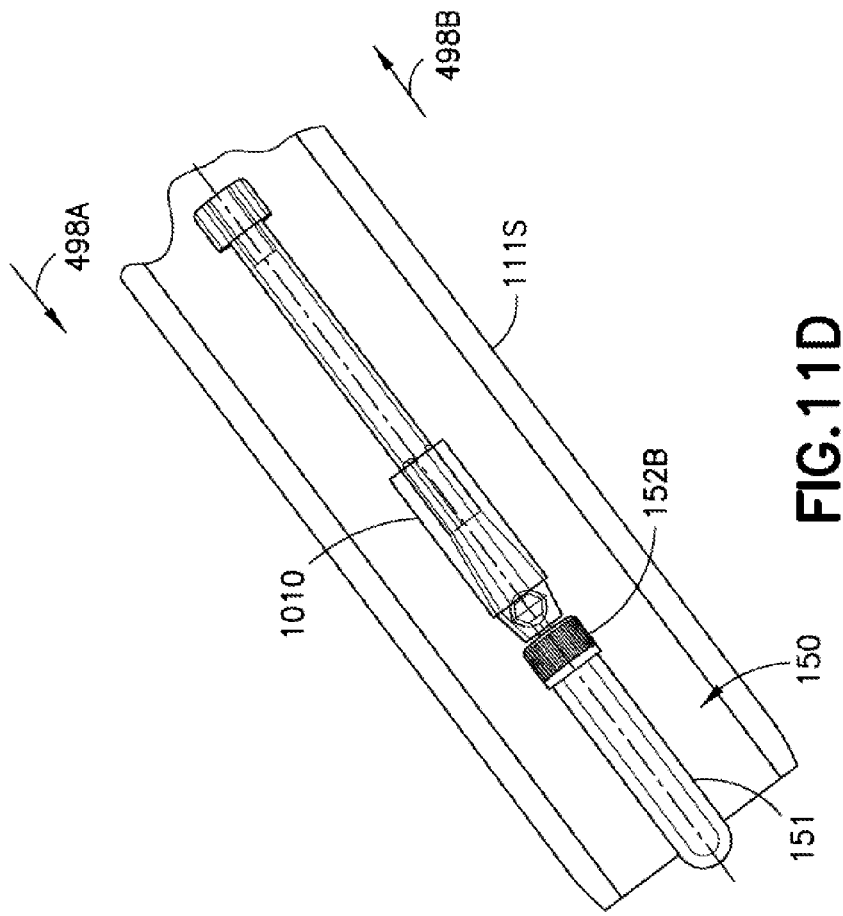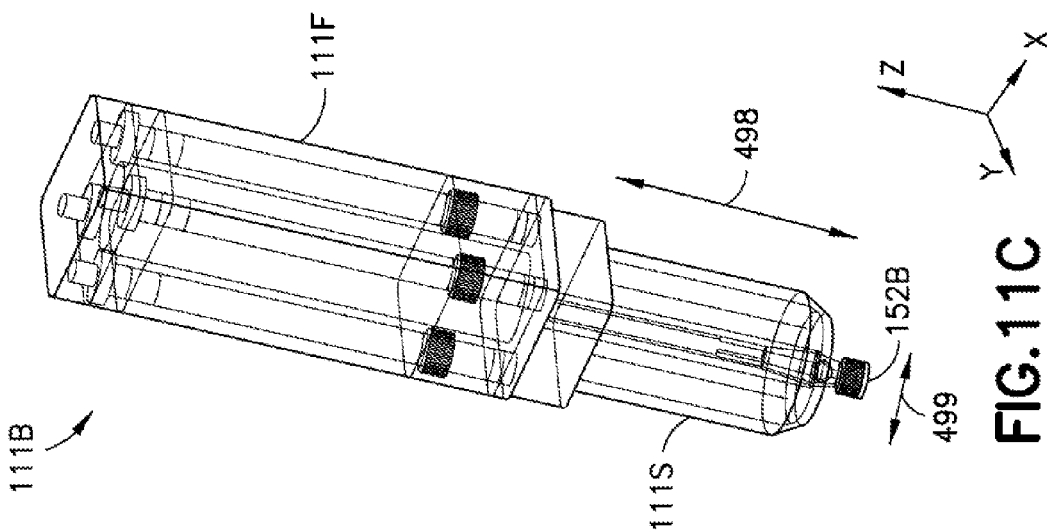

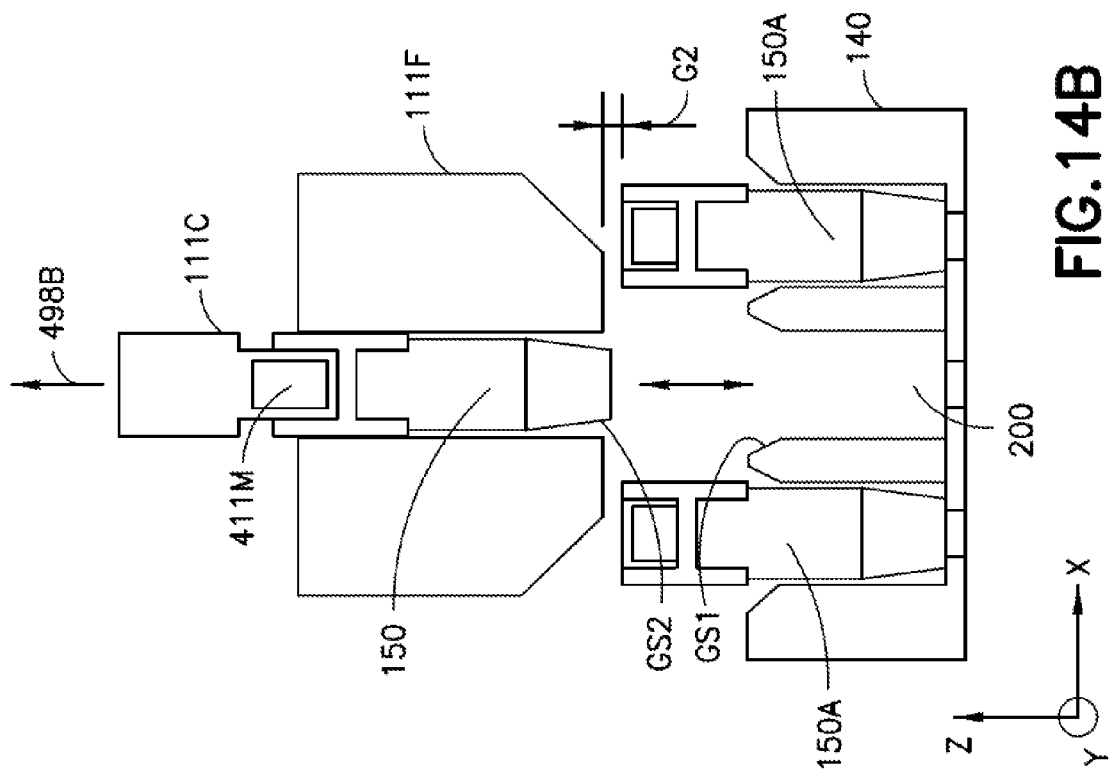
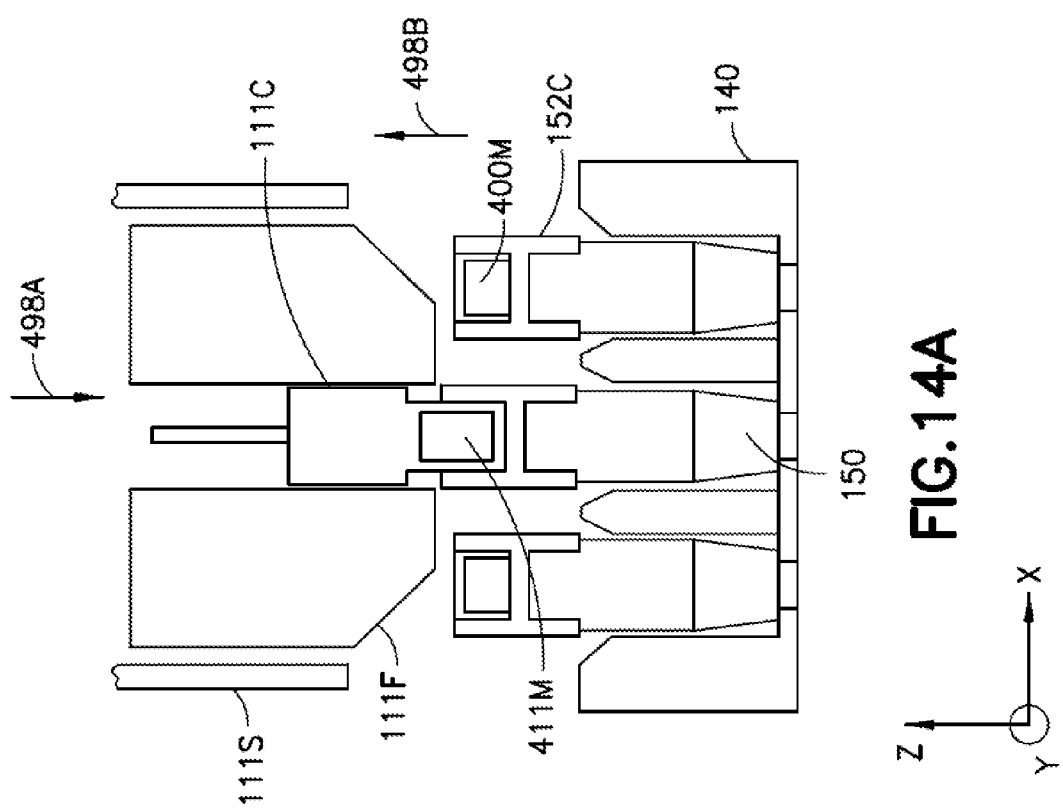

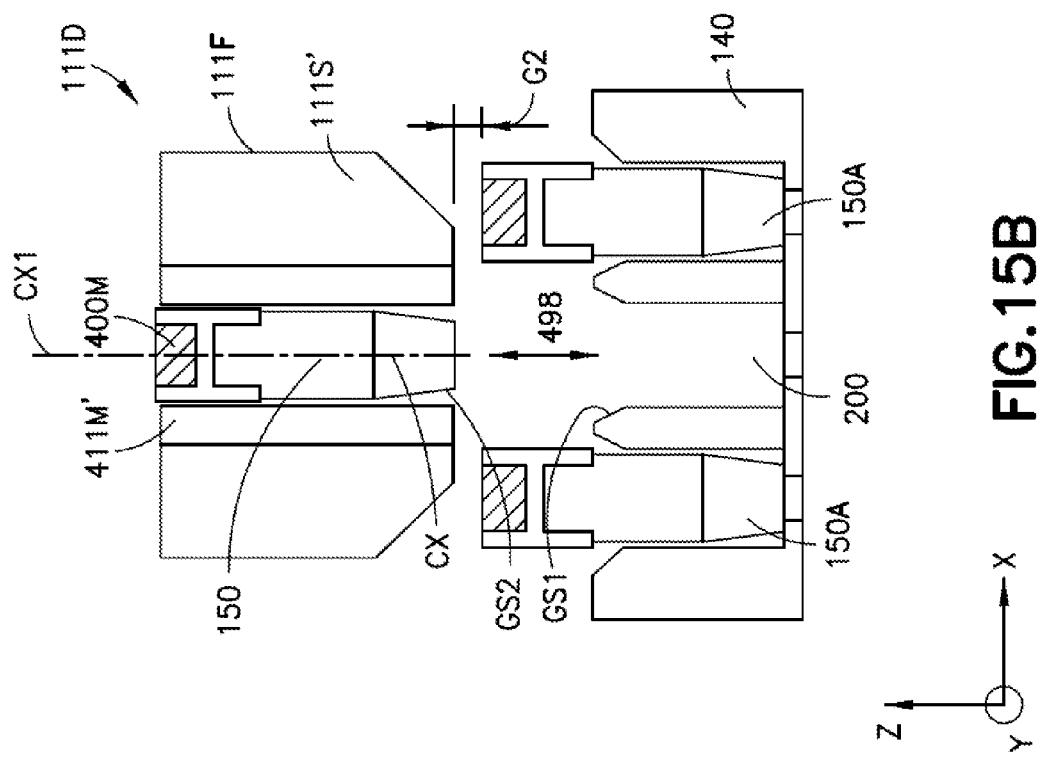
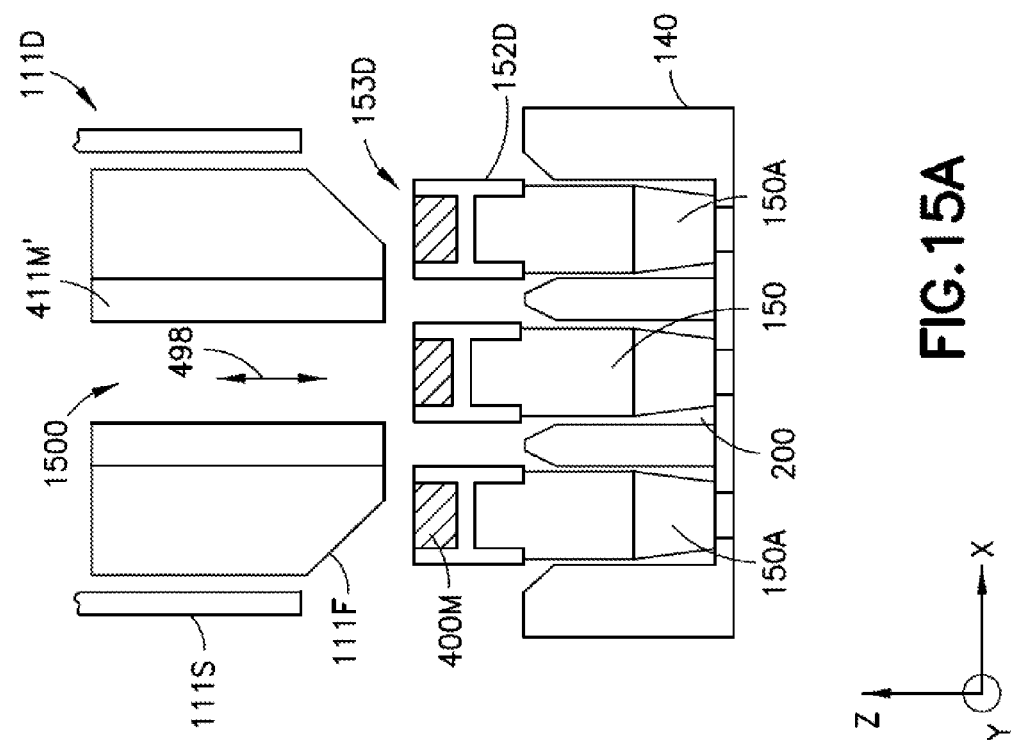
FIG. 15A
FIG. 15B

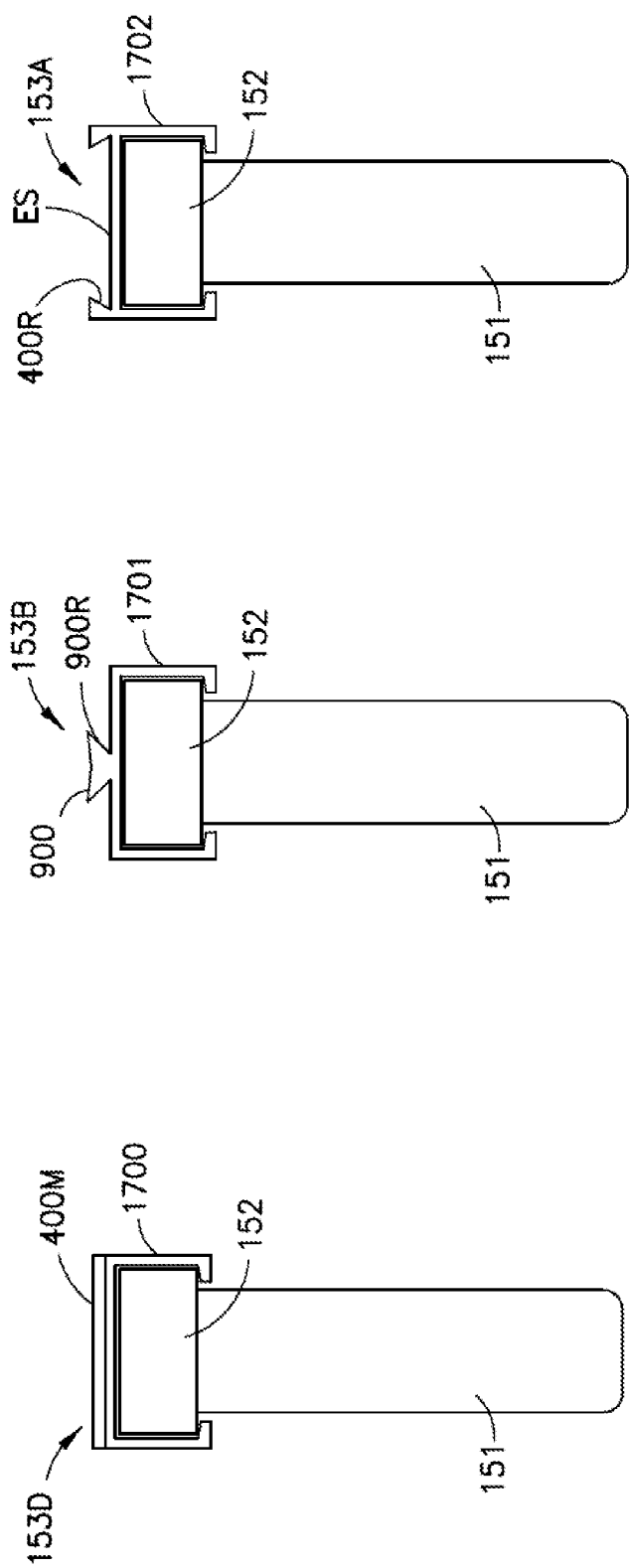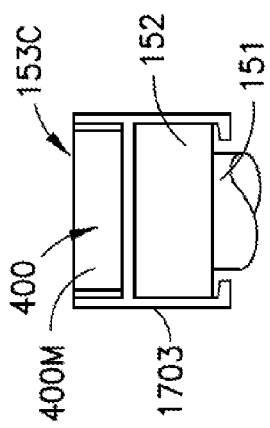

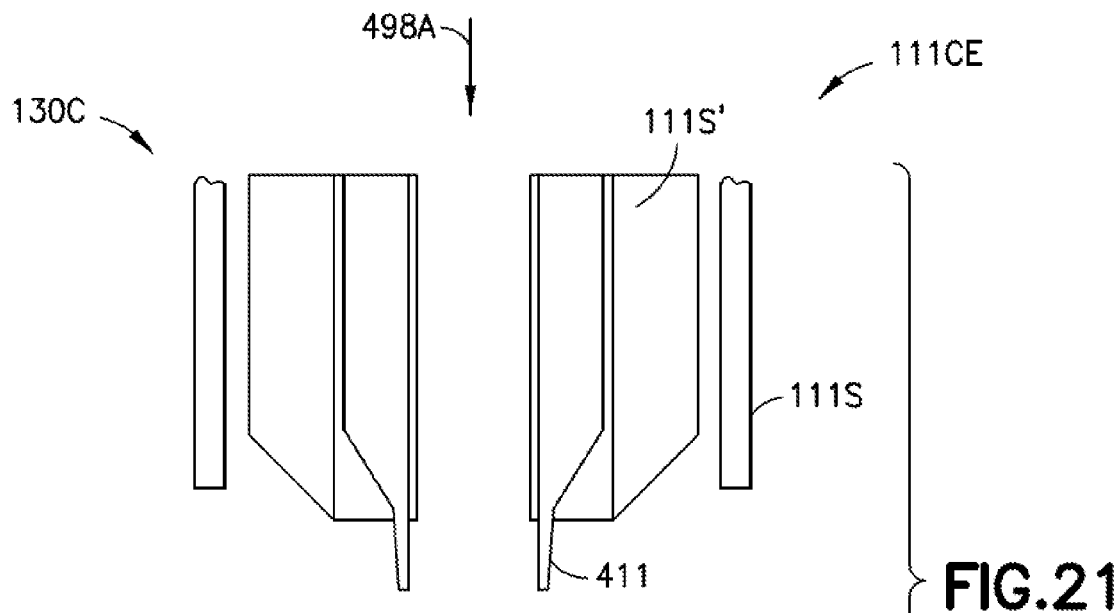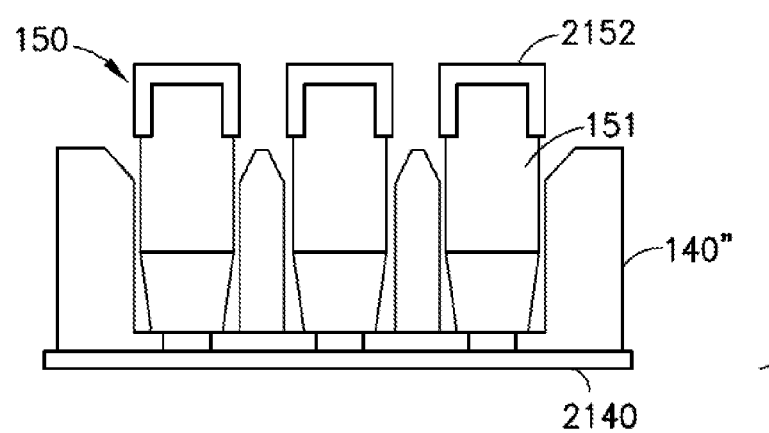
FIG.21

SAMPLE STORAGE AND RETRIEVAL SYSTEM

CROSS-REFERENCE TO RELATED APPLICATIONS

This application is a non-provisional of and claims the benefit of U.S. provisional patent application No. 61/971,646 filed on Mar. 28, 2014, the disclosure of which is incorporated by reference herein in its entirety.

BACKGROUND

1. Field

The exemplary embodiments generally relate to sample storage and retrieval systems and, more particularly, to the transfer and storage of samples.

2. Brief Description of Related Developments

Generally sample containers, such as test tubes are held in trays. Automated handling equipment may remove the sample containers from the trays for transport within, to or from a sample storage and retrieval system. Generally the automated handling equipment includes a gripper that grips the sample containers around an outside edge (e.g. outer peripheral side wall) of the sample container or around an outside edge (e.g. outer peripheral side wall) of a cap disposed on the sample container. A spacing between the outer peripheral walls of the sample containers within the trays is sized to accommodate at least a portion of the gripper extending between adjacent sample containers so that the sample containers may be gripped by the gripper for transport.

It would be advantageous to have a sample container gripper to sample container interface that does not extend between adjacent sample containers for picking/placing the sample containers from/to a sample container holding location. It would also be advantageous to be able to closely pack the sample containers within a tray so that an increased number of sample containers may be held and transported by the tray.

BRIEF DESCRIPTION OF THE DRAWINGS

The foregoing aspects and other features of the disclosed embodiment are explained in the following description, taken in connection with the accompanying drawings, wherein:

FIG. 1A is a schematic illustration of a sample container in accordance with aspects of the disclosed embodiment;

FIG. 1B is a schematic illustration of a sample container in accordance with aspects of the disclosed embodiment;

FIGS. 2A, 2B and 2C are schematic illustrations of a sample holder in accordance with aspects of the disclosed embodiment;

FIGS. 5A-5F are schematic illustrations of a portion of the sample storage and retrieval system and an operation thereof in accordance with aspects of the disclosed embodiment;

FIGS. 10A-10H are schematic illustrations of a portion of the sample storage and retrieval system and an operation thereof in accordance with aspects of the disclosed embodiment;

FIGS. 11A-11D are schematic illustrations of a portion of the sample storage and retrieval system in accordance with aspects of the disclosed embodiment;

FIGS. 14A and 14B are schematic illustrations of a portion of the sample storage and retrieval system and an operation thereof in accordance with aspects of the disclosed embodiment;

FIGS. 15A and 15B are schematic illustrations of a portion of the sample storage and retrieval system and an operation thereof in accordance with aspects of the disclosed embodiment;

FIGS. 17-20 are schematic illustrations of sample containers in accordance with aspects of the disclosed embodiment;

FIG. 21 is a portion of a cap exchange unit in accordance with aspects of the disclosed embodiment;

DETAILED DESCRIPTION

Figure 1:
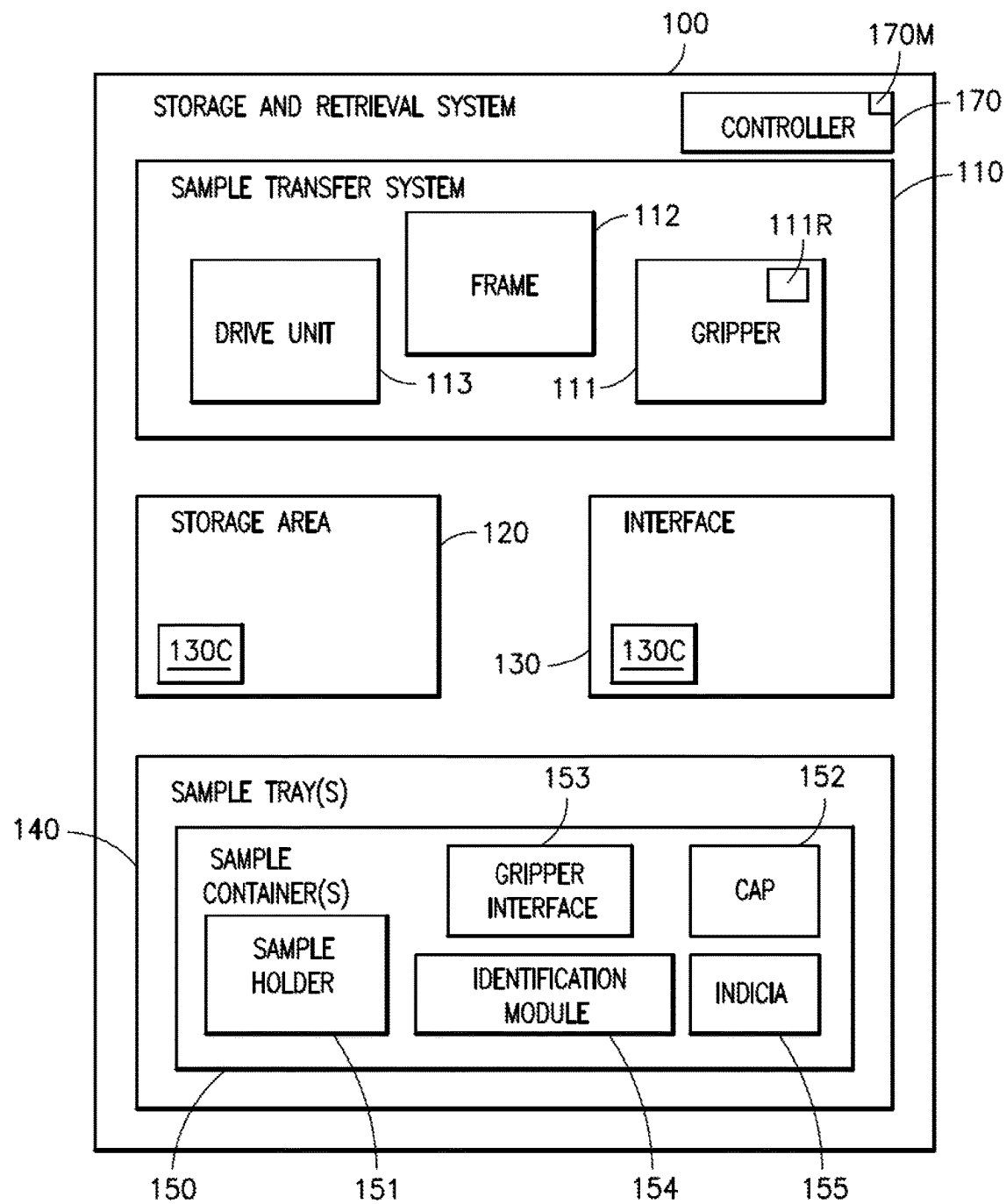
FIG. 1 is a schematic illustration of a sample storage and retrieval system in accordance with aspects of the disclosed embodiment.

FIG. 1 is a schematic illustration of a storage and retrieval system 100 in accordance with an aspect of the disclosed embodiment. Although the aspects of the disclosed embodiment will be described with reference to the drawings, it should be understood that the aspects of the disclosed embodiment can be embodied in many forms. In addition, any suitable size, shape or type of elements or materials could be used.

In one aspect the storage and retrieval system 100 includes any suitable interface 130, a storage area 120 and a sample transfer system 110. In one aspect the storage area 120 may be configured to maintain samples (e.g. biological samples or any other suitable samples) within sample containers 150 in an environment having any suitable temperature such as a room temperature environment, cold environments (e.g. −80° C.) and/or ultra-cold environments (e.g. −150° C.). It is noted that the sample containers described herein may be any suitable sample containers having any suitable size such as, for example, 2 ml cryovials and/or 1.4 ml cryotubes. The interface 130 may be configured to allow transfer of samples in one or more sample containers 150 and/or one or more sample trays 140 (e.g. holding the one or more sample containers 150) between an external environment outside the storage and retrieval system 100 and an environment within the storage and retrieval system 100. The interface 130 may also include a cap exchange unit 130C that removes a conventional cap from a sample container(s) holding a sample at a cold or ultra-cold temperature and installs a cap according to the aspects of the disclosed embodiment on the sample container(s) such that the sample remains insulated from convective heat exchange (e.g. warming of the sample) as will be described below. In other aspects the cap exchange unit may be located in any suitable portion of the storage and retrieval system such as in the storage area 120. In one aspect the sample transfer system 110 may be any suitable transfer system configured to transport one or more of sample storage trays 140 and sample containers 150 between the interface 130 and the storage area 120. The sample transfer system 110 may also be configured to pick and place (e.g. insert and remove) sample containers 150 from and to the sample trays 140. In one aspect the sample transfer system 110 may include any suitable frame 112, a drive unit 113 and a gripper 111 movably connected to the frame 112. The drive unit 113 may be configured to move the gripper 111 along one or more axis (X, Y and/or Z axes—see e.g. FIG. 2A) for transporting the sample containers 150 to and from the sample trays 140, to and from the interface 130 and/or to and from the storage area 120. The storage and retrieval system 100 may include any suitable controller 170 for controlling the operations of the sample transfer system 110 and the overall operation of the storage and retrieval system 100 as described herein.

Figure 2C:
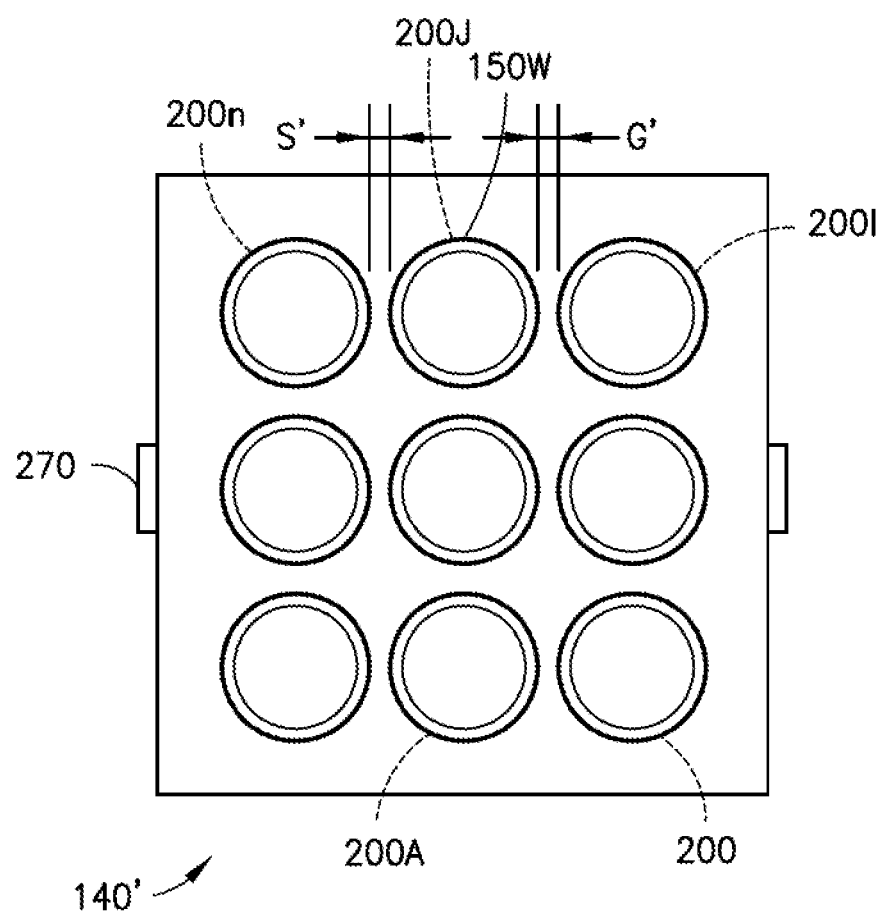

Referring to FIGS. 2A and 2B, each of the sample trays 140 may include a frame 140F and an array of sample container holding areas 200, 200A, . . . , 200I, 200J, . . . , 200n (generally referred to as sample container holding area(s) 200) disposed within the frame in, for example, a honeycombed arrangement (e.g. to provide a honeycombed array of sample containers 150). In other aspects, referring also to FIG. 2C, sample container holding areas 200, 200A, . . . , 200I, 200J, . . . , 200n of the sample trays 140' (which may be substantially similar to sample trays 140) may be disposed within the frame in, for example, an orthogonal arrangement (e.g. to provide an orthogonal array of sample containers 150) or in any other suitable arrangement. The sample container holding areas 200 may have any suitable shape and configuration for stably holding the sample containers 150 within the sample tray 140. Spacing S between adjacent sample container holding areas 200 may be independent of a gripping area 210 (e.g. that is disposed substantially within a perimeter 220 of a respective sample holding area) of the sample containers 150 held by the sample tray 140. The spacing S between the sample container holding areas 200 allows for a "closely packed" array of sample containers 150 where the term "closely packed" means that a gap G between adjacent sample container walls 150W is non-deterministic for gripper access of the adjacent sample holding containers 150. In one aspect the gap G may be such that the adjacent sample container walls 150W (e.g. such as the peripheral walls 152W of the cap 152 or the peripheral walls 151W of the sample holder 151) are in substantial contact or have only minimal clearance between the adjacent sample container walls 150W for allowing insertion and removal of the sample containers 150 to and from the sample tray 140. As may be realized, the spacing S' and gap G' of the orthogonally arranged tray 140' may be such that fewer sample containers are held by the tray 140' than are held by the sample tray 140 having the honeycombed sample container arrangement (e.g. the honeycombed arrangement has an increased storage density). The increased storage density of the closely packed array of sample containers may be effected by an over the cap gripper interface (as will be described further below) where the gripper 111 grips the sample container 150 from within the peripheral bounds of the cap 152. As may be realized, the over the cap gripper interface may also be used with the orthogonally arranged tray 140'.

In one aspect the sample container holding areas 200 may include any suitable sample container 150 retention features 250 for holding the sample containers 150 within the sample container holding areas 200. For example, the retention features 250 may be configured to mechanically, magnetically or otherwise engage the sample containers 150 in any suitable manner for holding the sample containers 150 in their respective sample container holding areas 200. As may be realized the holding force provided by the retention features may be overcome by the gripper 111 when removing and/or inserting the sample containers 150 from/to the sample tray 140. The sample tray 140 may also include one or more automation interfaces 270 configured to allow any suitable automated handling equipment to grip and transport the sample tray 140. In still other aspects the sample tray may include an aperture AP (see FIG. 9) through which a pushing member PM of the storage and retrieval system passes to lift and/or lower the samples to and from the gripper 111.

Referring again to FIG. 1 and also to FIG. 1A, each of the sample containers 150 may include a sample holder 151 and a cap 152 which may be constructed of any suitable materials. In one aspect the cap 152 may be constructed of any suitable plastic, glass filled plastic composite, rubber or any other suitable material. The sample holder 151 may include at least one peripheral wall 151W extending longitudinally along a central or longitudinal axis CX where the at least one peripheral wall 151W forms an opening 156 and a cavity 151C communicably connected to the opening 156. The at least one peripheral wall 151W may close the cavity 151C at one end so that the cavity 151C holds a sample(s) therein. Here the sample holder 151 is illustrated as having a cylindrical or test tube configuration but in other aspects the sample holder 151 may have any suitable configuration with any suitable number of peripheral walls. The sample holder 151 may include any suitable cap engagement portion 151P. The cap 152 may have any suitable configuration for engaging the sample holder 151 and closing the opening 156. In one aspect the cap 152 may have a cylindrical body 173 having at least one peripheral wall 152W forming an outer peripheral edge or side 152E of the cap 152 and defining the bounds within which the cap 152 (and hence the sample container 150) is gripped. In other aspects the body 173 may have any suitable shape and or configuration. The cap 152 may include a sample holder engagement portion 152P configured to interface with the cap engagement portion 151P for securing the cap 152 to the sample holder 151. In one aspect the sample holder engagement portion 152P may interface with the cap engagement portion 151P in any suitable manner such that the cap 152 is retained on the sample holder 151 through a frictional engagement, a threaded engagement (e.g., male or female threading), a snap engagement, a magnetic engagement or in any other suitable manner. A transport gripper interface 153 may be disposed on or within the cap substantially within the bounds of the outer peripheral edge or side 152E. In one aspect the transport gripper interface 153 may be of unitary construction with the cap 152 while in other aspects the transport gripper interface 153 may be a module coupled to the cap in any suitable manner (as will be described in greater detail below). The transport gripper interface 153 and the gripper 111 may form a self-centering interface as will be described below that may provide for accurate placement during sample container pick and place operations. It should be understood that while the aspects of the disclosed embodiment are illustrated in the figures with respect to a cap 152 that surrounds or is placed over the top of the sample holder 151 (e.g. male tube interface/female cap interface), in other aspects, referring to FIG. 1B, the sample holder 151 may surround the cap 152' (e.g. a female tube interface/male cap interface) such that the cap 152' is inserted into the opening 156 for retention within the opening in any suitable manner such as those described above with respect to interfaces 151P and 152P. The cap 152' which may be inserted into the opening 156 rather than over an outside periphery of the sample holder 151 may include a transport gripper interface 153 as described herein.

Figure 3C:
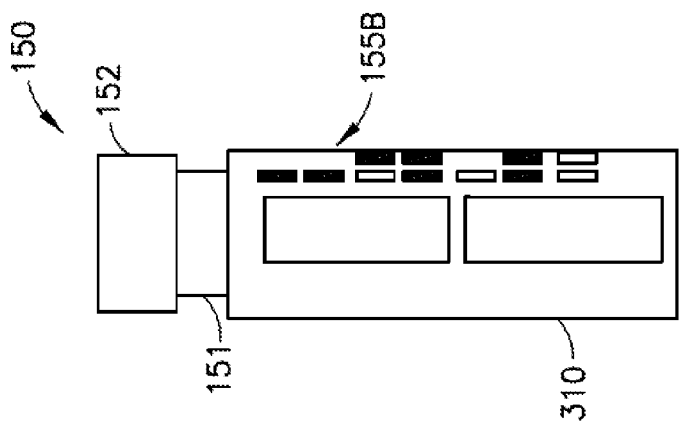
FIGS. 3A-3C are schematic illustrations of sample container marking features in accordance with aspects of the disclosed embodiment.
Figure 3B:
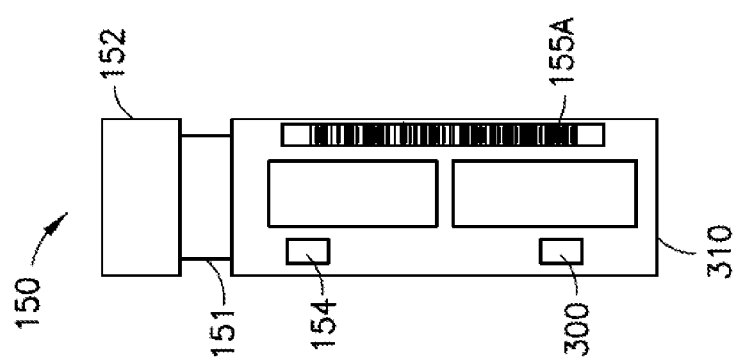
Figure 3A:
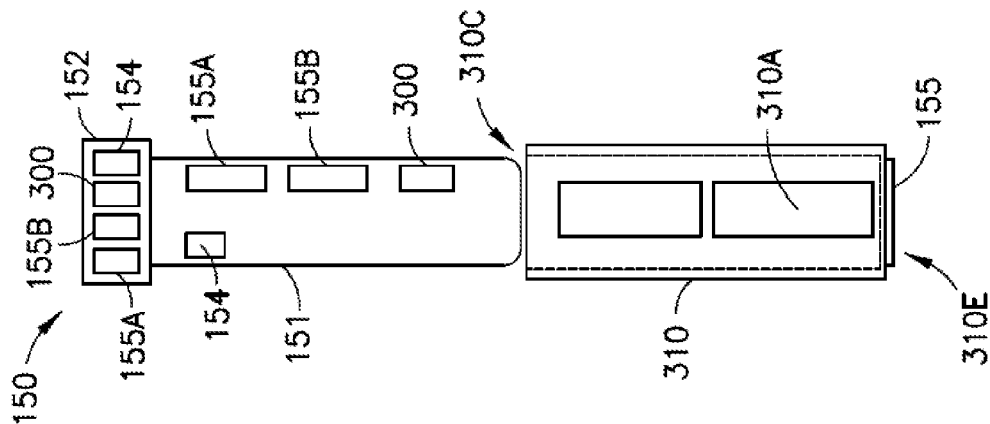

Referring also to FIGS. 3A-3B, in one aspect the sample container 150 may include one or more of an identification module 154 and identification indicia 155. The identification module 154 may be any suitable module configured to actively or passively provide information which may correspond to an identification of a sample within a respective sample container 150. In one aspect the identification module 154 may be a radio frequency identification module or tag or any other suitable radio frequency or wireless identifier. The identification module 154 may be disposed at least partly within the walls of (e.g. such as being molded within) or otherwise attached/coupled to (as will be described below) the cap 152 such that the transport gripper interface 153 and the identification module 154 are arranged relative to one another so that identification module 154 provides sufficient definition for identifying a respective sample container 150 when the sample container 150 is within an array of sample containers 150 such as when being held in the sample tray 140. The identification module 154 may be located on or within the cap 152 so as to be offset from the transport gripper interface 153. The location of the identification module 154 on or within the cap 152 may be such that the transport gripper interface 153 is exposed for over the cap access (e.g. the gripper accesses the cap/sample container from above the cap rather than on peripheral sides of the cap as will be described below). In one aspect the identification module may be read when, for example, the gripper 111 (which may include a reader module 111R for receiving information from the identification module) of the sample transfer system 110 passes over a respective sample container 150 and/or when the gripper 111 engages the transport gripper interface 153. In other aspects information may be obtained from the identification module in any suitable manner, at any suitable time and by any suitable identification reading device of the storage and retrieval system 100.

The identification indicia 155 may be one or more of any suitable bar code and data matrix. In one aspect the bar code may be a one dimensional or two dimensional barcode 155A or any other suitable visual identifier that may be machine or human readable and configured to identify and provide information about, for example, the sample within the sample container 150. In one aspect the data array may be a color array 155B or any other suitable visual identifier that may be machine or human readable and configured to identify and provide information about, for example, the sample within the sample container 150. As can be seen in FIGS. 3A-3C the identification indicia 155 (e.g. the barcode 155A and/or color array 155B) may be located on one or more of the sample holder 151, on the cap 152 and on a sleeve or jacket 310 that is configured such that at least a portion of the sample holder 151 is inserted into the sleeve 310. In one aspect the sleeve 310 includes a cavity 310C in which at least a portion of the sample holder 151 is inserted. The sleeve 310 may also include one or more apertures 310A configured to allow, for example, visual inspection of the sample within the sample holder 151. In one aspect the sleeve 310 includes a closed end 310E on which a barcode 155A may be placed or otherwise affixed (e.g. by printing, etching, mechanical or chemical attachment, etc.). In still other aspects one or more of the sleeve 310, the cap 152 and the sample holder 151 may include (e.g. affixed thereto or molded therein) any suitable temperature indicator or sensor 300, for example, one configured to indicate that a glass transition temperature or any other suitable predetermined temperature has been exceeded at least once for the sample within the sample holder 151 and/or for the sample holder 151. In some aspects, the temperature indicator is configured to indicate the current temperature of the sample and/or sample holder 151. In yet still other aspects one or more of the sleeve 310, the cap 152 and the sample holder 151 may include (e.g. affixed thereto or molded therein) an indicator of handling history, for example, one configured to indicate that the sample holder has exceeded a certain threshold shock or physical stress or that the sample holder has been opened or unsealed. One or both of the temperature indicator and the indicator of handling history can be configured to be read from directly observing one or more of the sleeve 310, the cap 152 and the sample holder 151 and/or can be configured to be read remotely via, for example, a wireless communication system or a remote imaging system. As can also be seen in FIGS. 3A-3C the identification module may also be located on the sample holder 151 and/or the sleeve 310 in addition to or in lieu of being located on the cap 152. It is noted that the indicia 155, the identification module 154 and/or the one or more indicators may be located on any suitable surface and/or located at least partly within a wall of the cap 152, the sample holder 151 and the sleeve 310.

Figure 4:
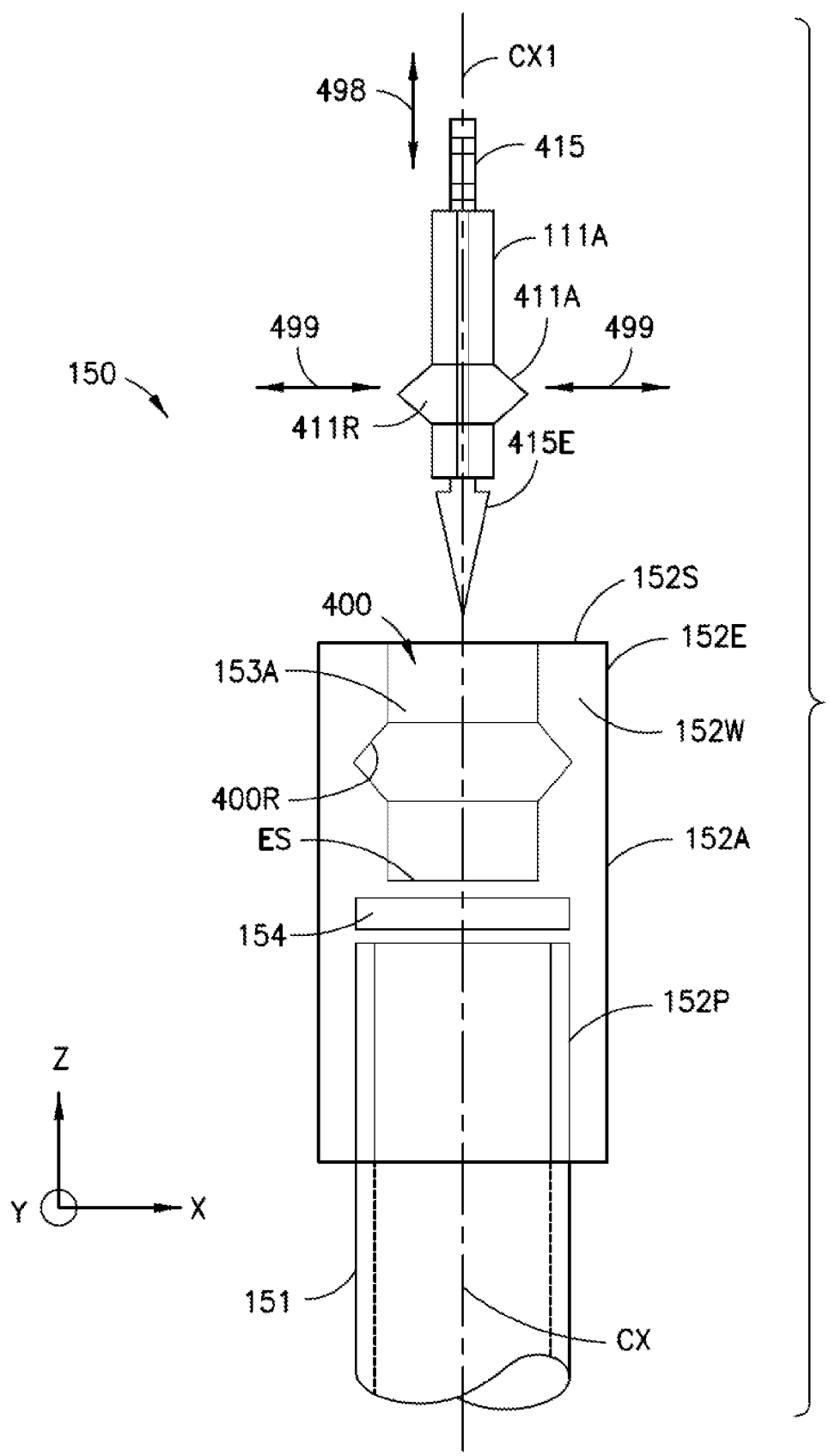
FIG. 4 is a schematic illustration of a portion of the sample storage and retrieval system in accordance with aspects of the disclosed embodiment.

Referring now to FIG. 4, in one aspect the cap 152A may be configured such that the transport gripper interface 153A is a mechanical interface formed on an interior or inside of the cap 152A. Here the transport gripper interface 153A is configured so that any suitable number of gripping members 411A of gripper 111A (which may be substantially similar to gripper 111 described herein) move outwards or away from each other relative to a centerline CX1 of the gripper 111A for interfacing with the transport gripper interface 153A (see FIG. 2A). For example, transport gripper interface includes a cavity or recess 400 having an opening in a surface 152S (such as a top surface disposed opposite the sample holder engagement portion 152P) of the cap 152A. The cavity 400 may include at least one internal side wall configured to engage gripper 111 such that mechanical forces exerted by the gripper 111 on the at least one internal side wall radiate from longitudinal axis CX. In one aspect one or more retention features 400R may be located in or on the at least one internal sidewall and be configured to positively interface with the gripper 111. In some aspects one or more retention features 400R are configured to interface with the gripper 111 and/or a cap securing/removal system, such as cap exchange unit 130C described herein, so as to permit rotation of the cap relative to the sample holder. In other aspects the cap contains one or more additional features, for example, a texture or ribbing on the peripheral wall 152W or within cavity 400, configured to interface with the gripper 111 and/or cap exchange unit 130C so as to permit rotation of the cap relative to the sample holder. As can be seen in FIG. 4, the transport gripper interface 153A is disposed within the bounds of the peripheral wall 152W (e.g. does not extend past the edge or side 152E of the peripheral wall 152W) and as such, the transport gripper interface 153A is disposed within the perimeter 220 of a respective sample holding area of the sample tray 140 when the sample container 150 is disposed within the sample tray 140. The gripper 111A may include one or more fingers or gripping members 411A that are moveable in the direction of arrows 499 (see also FIG. 2A). The gripping members 411A may be constructed of any suitable material such as for example, stainless steel, carbon fiber or any other suitable stiff material. In other aspects the gripping members may be constructed at least partly of a resilient material as will be described below. The gripping members 411A may include retention features 411R that are configured to engage retention features 400R of the cap 152A, e.g. when the gripping members 411A are moved in the direction of arrows 499 (e.g. towards the peripheral wall(s) 152W or away from the longitudinal axis CX of the sample container 150) where engagement of the retention features 411R with retention features 400R at least in part align the longitudinal axis CX1 of the gripper 111A with the longitudinal axis CX of the sample container 150 (e.g. the interface between the sample container and the gripper is a self-centering interface). Engagement of the retention features 411R with retention features 400R may provide positive gripping of the sample container 150 by the gripper 111A. The gripper 111A may include an ejector member 415 configured at least in part disengage the sample container 150 from the gripper 111A. The ejector member 415 may be movable in the direction of arrow 498 relative to the gripping members 411A so that as the gripping members 411A move away from the peripheral wall(s) 152W the ejector member 415 pushes on an ejection surface ES of the cavity 400 so that the sample container 150 is moved off of the gripper 111A and/or the gripper is lifted out of the cavity 400.

Figure 6:
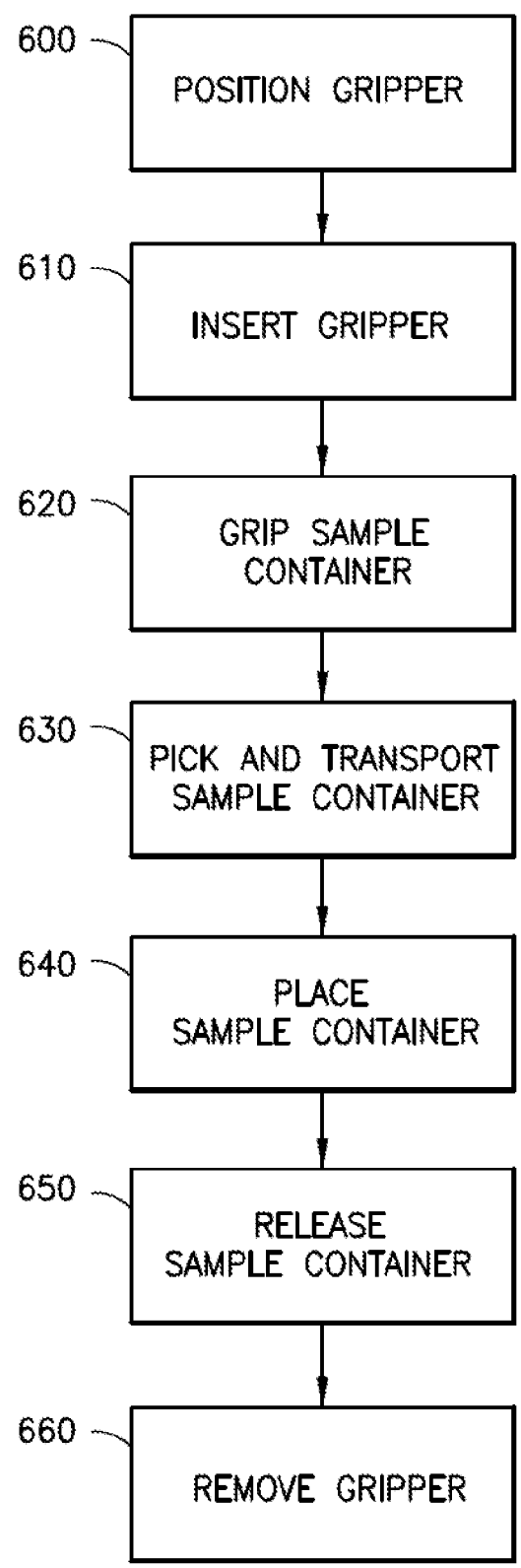
FIG. 6 is a flow diagram in accordance with aspects of the disclosed embodiment.

Referring also to FIGS. 1, 5A-5F and FIG. 6 a picking/placing operation of the sample container 150 will be described. The controller 170 may position, using the drive unit 113, the gripper 111A above a predetermined sample container 150 disposed within, for example, a sample tray 140 or any other suitable sample container holding area (FIG. 6, Block 600). In one aspect the controller 170 may identify the predetermined sample container 150 using one or more of the identification module 154 and a look up table in a memory 170M accessible by the controller where the look up table tracks a location of the samples within the storage and retrieval system 100 or in any other suitable manner. The gripper 111A is moved in the direction of arrow 498A to position the gripping members 411A within the cavity 400 and to align the retention features 411R of the gripper 111A with the retention features 400R of the cap 152A (FIG. 6, Block 610). The retention features 411A of the gripper 111A may be moved in the direction of arrow 499 towards the peripheral wall(s) of the cap 152A so that the retention features 411R engage the retention features 400R and the gripper 111A grips the sample container 150 (FIG. 6, Block 620). In one aspect the drive unit 113 of the sample transfer system 110 may be configured to extend and retract the gripping members 411A in any suitable manner. In one aspect the ejector member 415 may be employed to extend and retract the gripping members 411A. For example, the ejector member 415 may be biased (in any suitable manner such as by a resilient member similar to resilient member 711—FIG. 7A) in the direction of arrow 498B and the gripping members 411A may be biased (in any suitable manner such as by resilient member 710—FIG. 7A) in a retracted or non-extended position. The ejector member 415 may include an extender portion 415E that when positioned between the gripping members 411A causes the extension or spreading of the gripping members 411A in the direction of arrow 499. As may be realized, the bias of the ejector member 415 in the direction of arrow 498B may position the extender portion 415E relative the gripping members 411A (e.g. so that the gripping members are in the retracted position) allows any sample container 150 held by the gripper 111A to remain held by the gripper 111A in the event of a power failure. In still other aspects the gripping members 411A may be opened and closed by a respective portion of the drive unit 113 configured to move each of the gripping members in the direction of arrow 499 independent of the ejector member 415. Once the sample container 150 is gripped by the gripper 111A the controller may cause, using the drive unit 113, the sample 150 to be picked from the sample container holding area and transferred from/to the sample tray 140 or from/to any other suitable sample container holding area (FIG. 6, Block 630). The sample container may be positioned over a predetermined sample holding location, such as a sample container holding area 200 and placed into the holding area (FIG. 6, Block 640). The drive unit 113 may effect relative movement of the ejector member 415 and the gripping members 411A so that the ejector member 415 is moved in the direction of arrow 498A while the gripping members 411A are moved in the direction of arrow 498B to open the gripping members 411A and release the sample container 150. In other aspects the ejector member 415 may be held stationary against the ejection surface ES while the gripping members 411A are moved in the direction of arrow 498B to open the gripping members 411A and release the sample container 150. As may be realized, the relative movement of the gripping members 411A and the ejector member 415 causes movement of the gripping members 411A in the direction of arrow 499 away from the peripheral wall(s) 152W to release the retention members 411R from the retention members 400R (FIG. 6, Block 650). As the gripping members 411A (and the gripper 111A) are removed from cavity 400 (FIG. 6, Block 660) the ejector member 415 may hold the sample container 150 within the sample holding area or otherwise move the sample container 150 off of the gripper 111A.

Figure 7A:
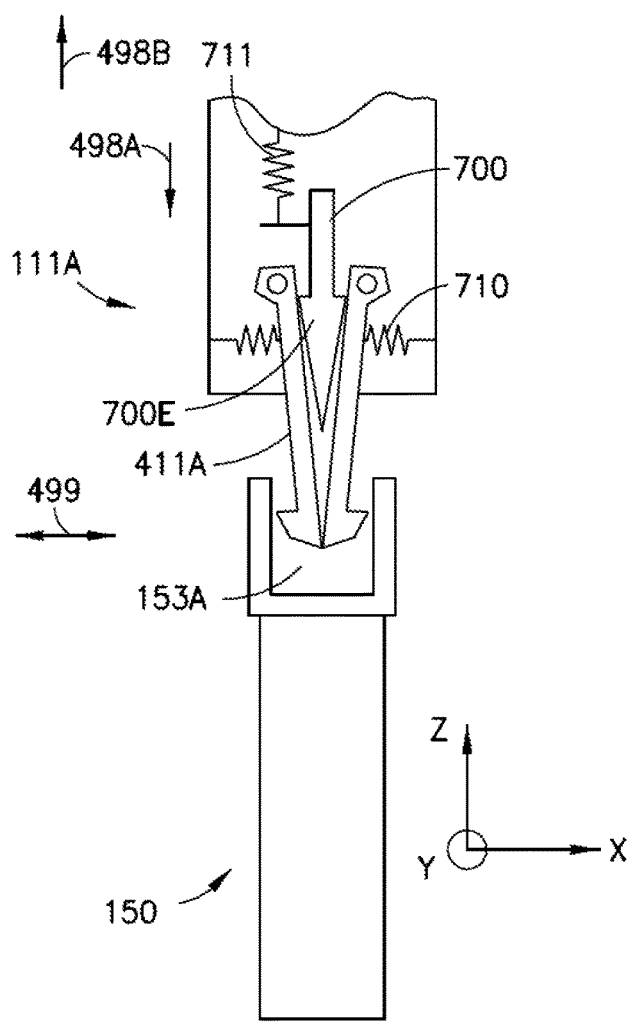
FIGS. 7A and 7B are schematic illustrations of a portion of the sample storage and retrieval system and an operation thereof in accordance with aspects of the disclosed embodiment.
Figure 7B:
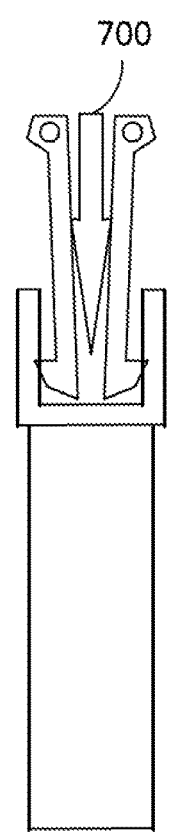

Referring to FIGS. 7A-7B, in one aspect, the actuation of the gripping members 411A may be independent of the ejector member 415 or where an ejector member 415 is not provided. For example, a transmission member 700 may be connected to the drive unit 113 for movement in the direction of arrows 498A, 498B. The transmission member 700 may include an extender portion 700E, substantially similar to extender portion 415E described above, such that when the transmission member 700 is moved in the direction of arrow 498A to a position between the gripping members 411A the gripping members 411A are moved, by the extender portion 700E, in the direction of arrow 499 to engage the retention features 400R of the cap 152A in a manner substantially similar to that described above. As may be realized, the sample container 150 may be released from the gripper 111A by moving the transmission member 700 in the direction of arrow 498B relative to the gripping members 411A (which may be biased in a retracted position) so that the gripping members move away from the peripheral wall(s) of the cap 152A in a manner substantially similar to that described above. The gripping members 411A may be biased in a retracted position in any suitable manner such as by a resilient member 710 and the transmission member 700 may be biased in the direction of arrow 498A by any suitable resilient member 711 so that the transmission member causes extension of the gripping members 411A and the gripping members are extended or remain extended in the event of a power failure so that any sample container held by the gripper 111A remains held by the gripper 111A.

Figure 8A:
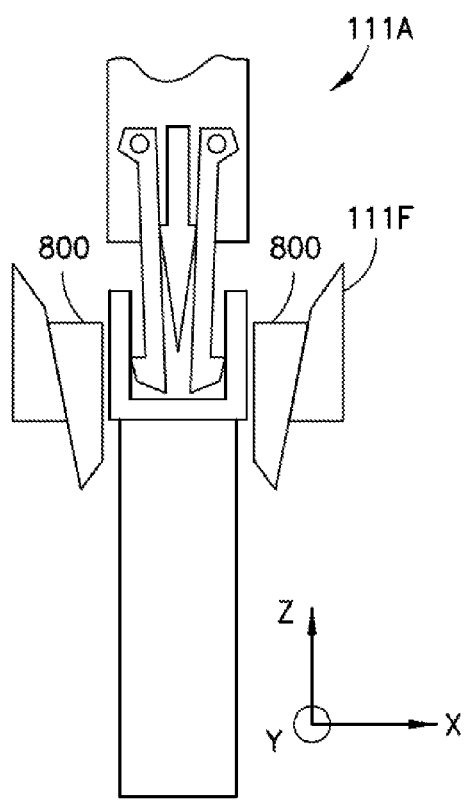
FIGS. 8A and 8B are schematic illustrations of a portion of the sample storage and retrieval system and an operation thereof in accordance with aspects of the disclosed embodiment.
Figure 8B:
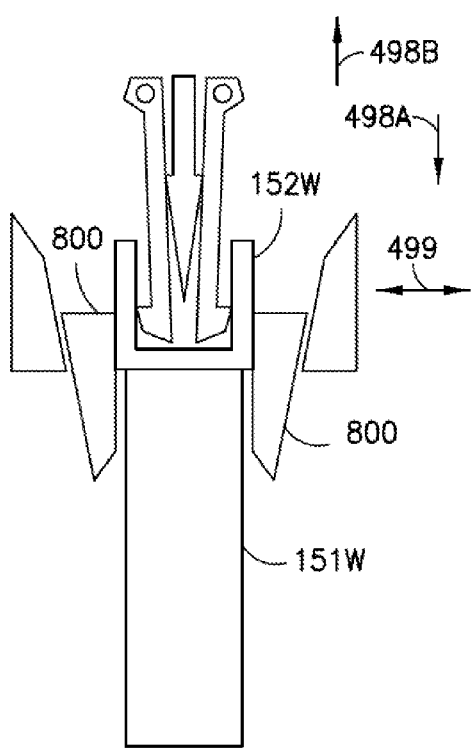

Referring also to FIGS. 8A and 8B the gripper 111A includes a frame 111F to which one or more of the gripping members 411A, the ejector member 415 and the transmission member 700 are connected. It is noted that in one aspect both an ejector member 415 and transmission member 700 may be included in the gripper 111A while in other aspects one of the ejector member 415 or the transmission member 700 may be included in the gripper 111A. The frame 111F may include sample container interface members 800 for further gripping, centering and/or stabilizing the sample container 150 relative to the frame 111F. While the sample container interface members 800 are illustrated as pivoting members, for exemplary purposes, in other aspects the sample container interface members 800 may be any suitable guide surfaces for stabilizing the sample container 150. In one aspect the sample container interface members 800 may be a resilient member disposed within a channel of the frame 111F in which the sample container is at least partially disposed when carried by the gripper. The sample container interface members 800 may stabilize and/or center the sample container within the frame 111F during transport of the sample container 150. For example, in one aspect the sample container interface members 800 may be positioned around a sample container disposed at least partly within the frame or otherwise located adjacent the frame. In one aspect the gripper 111A may be configured to transport the sample container at least partly within the frame 111F while in other aspects the gripper 111A may be configured so that the sample container is held adjacent the frame (e.g. such as below) the frame 111F. The sample container interface members 800 may be moved in any suitable direction(s), such as directions 498A, 499 so as to be positioned against the peripheral wall(s) of at least one of the cap 152A and the sample holder 151 for stably holding the sample container 150 during transport. As may be realized, the sample container interface members 800 may be moved in the direction(s) of arrow 498B, 499 so as to be positioned away from the peripheral wall(s) of at least one of the cap 152A and sample holder 151 for allowing relative movement between the sample container 150 and the frame 111F.

Figure 10A:
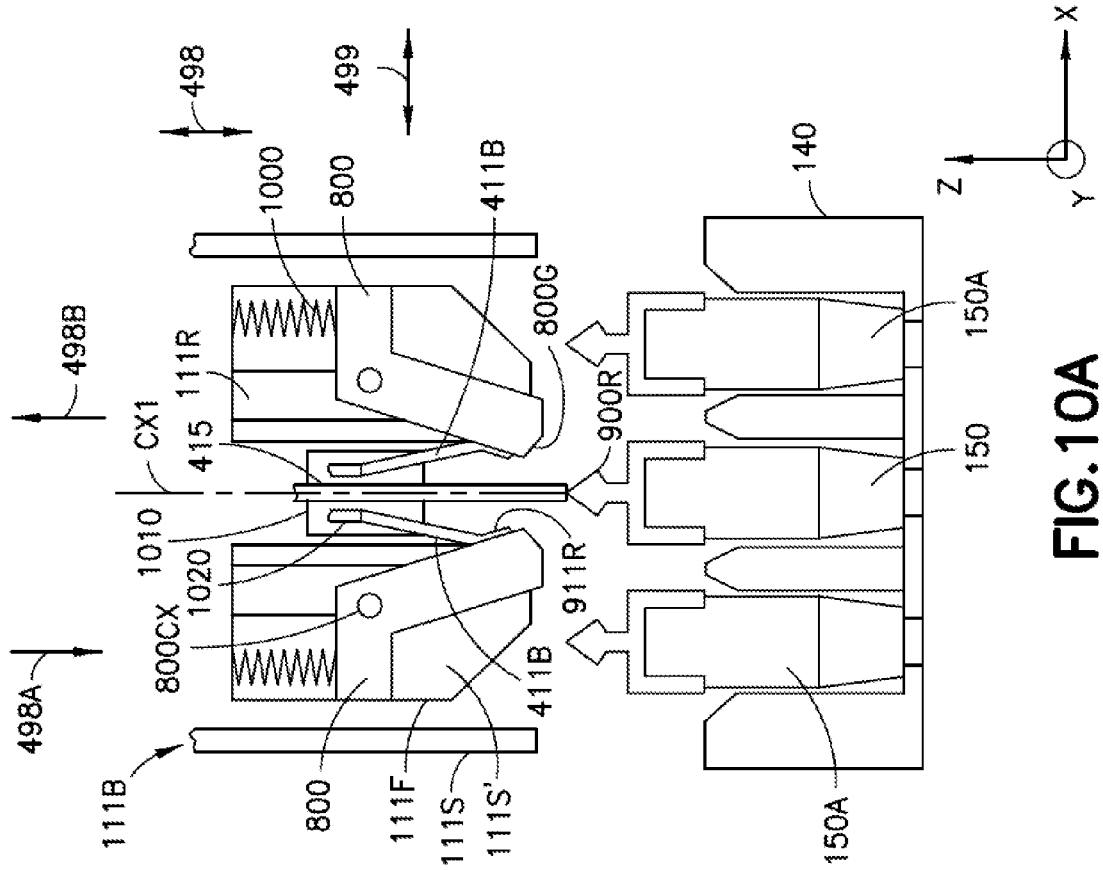
Figure 9:
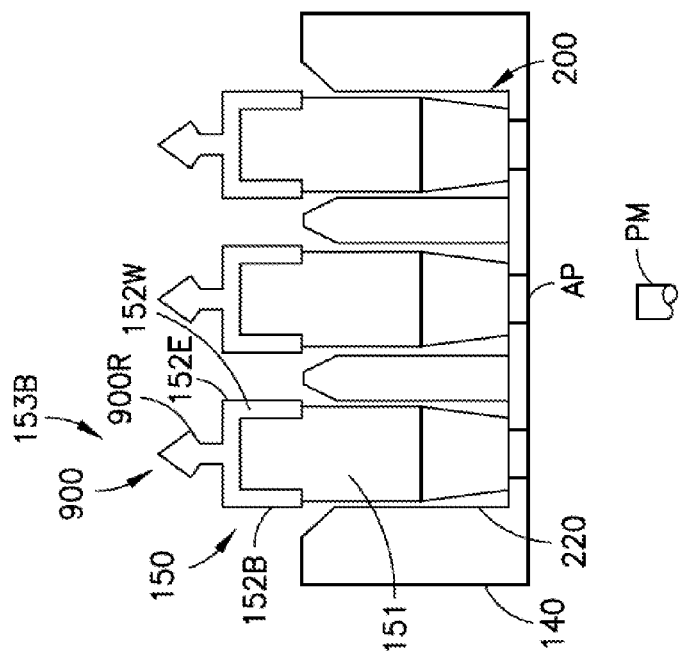
FIG. 9 is a schematic illustration of a sample container in accordance with aspects of the disclosed embodiment.
Figure 10F:
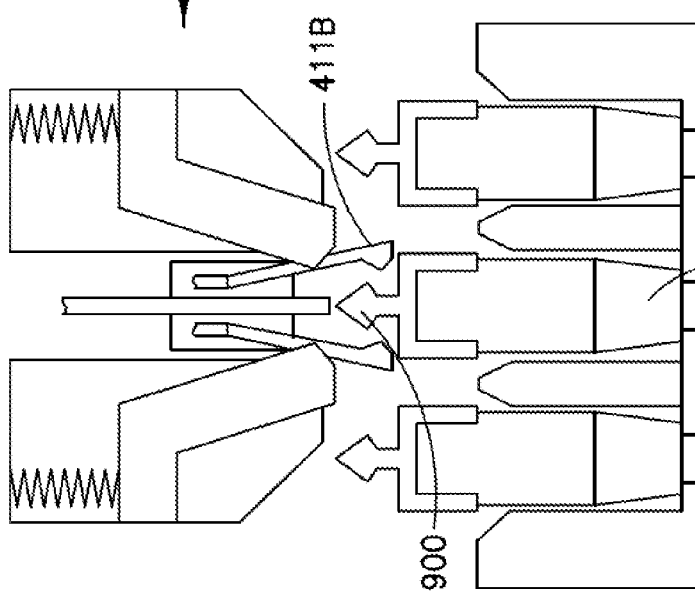
Figure 10G:
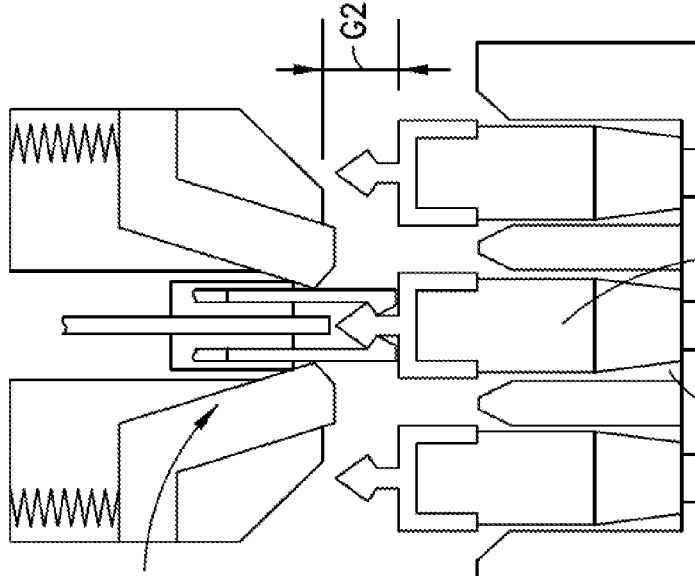
Figure 10H:
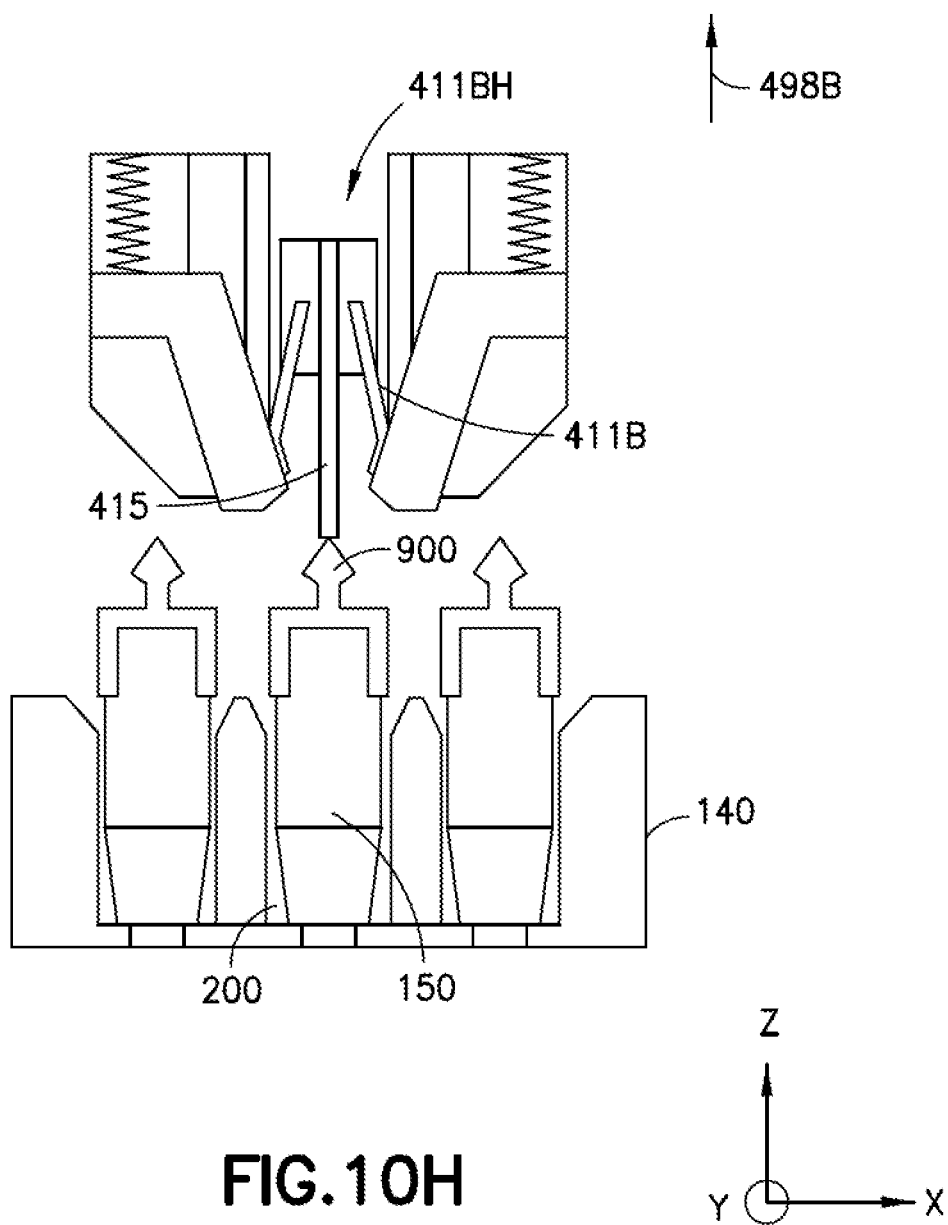

Referring now to FIG. 9, in one aspect the cap 152B may be configured such that the transport gripper interface 153B is a mechanical interface formed on an exterior or surface 152S of the cap 152B. In this aspect the surface 152S is a top surface of the cap (e.g. a surface disposed opposite the sample holder 151). Here the transport gripper interface 153B is configured so that any suitable number of gripping members 411B of gripper 111B (which may be substantially similar to gripper 111, 111A described herein) move inwards or towards each other relative to a centerline CX1 (FIG. 10A) of the gripper 111B for interfacing with the transport gripper interface 153B (see FIG. 2B). For example, transport gripper interface 153B includes a protrusion 900 extending from the surface 152S of the cap 152. The protrusion 900 may include one or more retention features 900R configured to positively interface with the gripper 111B. The retention features 900R and/or the gripper members 411B may include guide surfaces GS3, GS4 which may provide self-alignment between the gripping members 411B and the protrusion 900 as the gripping members 411B are moved over/past the retention features 900R when picking the sample container 150 (e.g. for engaging the protrusion). In some aspects one or more retention features 900R are configured to interface with the gripper 111B and/or cap exchange unit 130C so as to permit rotation of the cap relative to the sample holder. In other aspects the cap contains one or more additional features, for example, a texture or ribbing on the peripheral wall 152W or on protrusion 900, configured to interface with the gripper 111B and/or cap exchange unit 130C (or a hand/fingers of a manual operator) so as to permit rotation of the cap relative to the sample holder (as will be described in greater detail below). As can be seen in FIG. 9, the transport gripper interface 153B is disposed within the bounds of the peripheral wall 152W (e.g. does not extend past the edge or side 152E of the peripheral wall 152W) and as such, the transport gripper interface 153 is disposed within the perimeter 220 of a respective sample holding area of the sample tray 140 when the sample container 150 is disposed within the sample tray 140. Referring also to FIG. 10A the gripper 111B may include one or more fingers or gripping members 411B that are moveable in the direction of arrows 499 (see also FIG. 2B). The gripping members 411B may include retention features 911R that are configured to engage retention features 900R of the cap 152B, e.g. when the gripping members 411B are moved in the direction of arrows 499 (e.g. away from the peripheral wall(s) 152W towards the longitudinal axis CX of the sample container 150). Engagement of the retention features 911R with retention features 900R may at least in part align the longitudinal axis CX1 of the gripper 111B with the longitudinal axis CX of the sample container 150 (e.g. the interface between the sample container and the gripper is a self-centering interface). Engagement of the retention features 911R with retention features 900R may also provide positive gripping of the sample container 150 by the gripper 111B. The gripper 111B may include an ejector member 415 configured at least in part to disengage the sample container 150 from the gripper 111B in a manner substantially similar to that described above. As described above, the ejector member 415 may be movable in the direction of arrow 498 relative to the gripping members 411B so that the as the gripping members 411B move towards the peripheral wall(s) 152W the ejector member 415 pushes on the protrusion 900R so that the sample container 150 is moved off of the gripper 111B and/or the gripper is lifted from the sample container 150. In one aspect the gripping members 411B may be opened and closed in a manner substantially similar to that described above with respect to gripping members 411A while in other aspects the gripping members 411B may be opened and closed in any suitable manner, such as that described below. In still other aspects the gripping members 411B may be opened and closed by a respective portion of the drive unit 113 configured to move each of the gripping members in the direction of arrow 499 independent of the ejector member 415.

Still referring to FIG. 10A and also to FIGS. 11A-11D the gripper 111B includes a frame 111F to which the gripping members 411B and the ejector member 415 are connected. In one aspect the gripping members 411B may have a dual bias. For example, at least a portion of the gripping members 411B may be resilient where the gripping members 411B extend or otherwise depend from a body 1020. The gripping members 411B may be biased away from each other (e.g. in an open position) such that the gripping members 411B are spread apart or otherwise extend away from the longitudinal axis CX1 of the gripper 111B. In one aspect the body 1020 may be movable relative to a grip tube 1010 that is connected to the frame 111F and through which the body 1020 passes, where the body 1020 may be biased in the direction of arrow 498B so that the gripping members 411B are pulled at least partially into the grip tube 1010 for closing the gripping 411B. An interaction between the gripping members 411B and the grip tube 1010 as the body 1020 is moved in the direction of arrow 498B causes the gripping members 411B to move towards each other (e.g. towards the longitudinal axis CX1 to place the gripping members in a gripping position) for gripping the sample container 150. As may be realized, the interaction between the gripping members 411B and the grip tube 1010 as the body 1020 is moved in the direction of arrow 498A causes the gripping members 411B to move away from each other (e.g. away from the longitudinal axis CX1 to place the gripping members in an open or un-gripped position) for allowing the gripping members 411B to pass over the retention features 900R for picking and placing the sample containers 150. In another aspect, the grip tube 1010 may be movable relative to the body 1020 where the tube 1010 may be biased in the direction of arrow 498A for holding the gripping members 411B in the gripping position and for opening the gripping members 411B when the grip tube is moved in the direction of arrow 498B. In other aspects the body 1020 (and hence the gripping members 411B) and the grip tube 1020 may be movable relative to each other. As may be realized, the bias of the grip tube 1010 and/or gripping members 411B may hold the gripping members 411B in a closed position in the event of, for example, a power failure so that a sample container 150 held by the gripper 111B remains held by the gripper 111B. In another aspect, the gripper 111B may not include the grip tube 1010 and gripping members 411B may be opened or otherwise spread apart using an ejector member 415 in a manner substantially similar to that described above, where the ejector member passes between the gripping members 411B to spread or otherwise open the gripping members 411B.

The frame 111F may include sample container interface members 800 for further gripping, centering and/or stabilizing the sample container 150 when held by the gripper 111B. The sample container interface members 800 may stabilize and/or center the sample container within the frame 111F during transport of the sample container 150 in a manner substantially similar to that described above. In this aspect the sample container interface members 800 may be pivotally mounted to the frame 111F about a respective pivot axis 800CX so that a gripping portion 800G of the sample container interface members 800 is biased towards the longitudinal axis CX1 of the gripper 111B in any suitable manner, such as by resilient members 1000.

In one aspect the frame 111F described herein may form a sleeve 111S' and/or otherwise include a sleeve 111S mounted to the frame 111F. In some aspects, the sleeve 111S, 111S' is sized and shaped to substantially prevent sample containers 150A adjacent to a predetermined sample container 150 being picked from moving out of their respective sample holding area 200 of, e.g. the sample tray 140, when the gripper 111B accesses predetermined sample container 150. For example, sleeve 111S, 111S' may be movable relative to the gripping members 411B and positioned, during picking and placing sample containers, proximate to the adjacent sample containers 150A so that there is insufficient room above the adjacent sample containers 150A for the adjacent sample containers 150A to be moved out of respective sample holding areas 200 of, for example, sample tray 140. Sleeve 111S, 111S' may be constructed of any suitable material such as a plastic, metal or composite. In some aspects, sleeve 111S, 111S' is constructed of an insulating material and/or a radiation blocking material. In some aspects, gripper 111B and/or sleeve 111S, 111S' is constructed to prevent convective heat transfer and/or radiation exposure as the sample container 150 is moved from one location to another. For example, gripper 111B and/or sleeve 111S, 111S' can be constructed to reduce or minimize air movement across sample container 150 during movement of the container between sample holding areas 200. In some aspects, sample container 150 is drawn mostly or completely within gripper 111B and/or sleeve 111S, 111S' prior to movement to a new sample holding area 200. In one aspect the gripper 111B and/or sleeve 111S, 111S' may include refrigeration such as, for example, a heat transfer loop or reservoir 111R configured to hold any suitable refrigerant, such as liquid nitrogen or any other suitable heat transfer fluid, for cooling a sample container 150 held by the gripper 111B. Sleeve 111S, 111S' may be movable in the direction of arrow 498 relative to the frame 111F so that the sleeve 111S can be positioned around a sample container 150 held by the gripping members 411B (see FIG. 11D) and/or for actuation of the gripping members 411B as described herein. In one aspect, movement of the sleeve 111S, 111S' may actuate the gripping members 411B such that movement of the sleeve may be coupled to the movement of the grip tube 1010. In one aspect, as the sleeve 111S, 111S' moves in the direction of arrow 498A the grip tube 1010 may move with the sleeve until the grip tube engages the gripping members 411B and the gripping members grip the protrusion 900. The sleeve 111S, 111S' may continue to move (e.g. where the grip tube is held against the gripping members in any suitable manner such as by a biasing force or biasing member connected between the grip tube and the insulated sleeve) in the direction of arrow 498A so that the sample container 150 held by the gripping members is at least partially within the insulated sleeve 111S, 111S'. In one aspect the sample container interface members 800 may be integrated into the sleeve while in other aspects the sleeve may be formed or otherwise integrated into the sample container interface members 800 (e.g. where the sample container interface members 800 may include the reservoir 111R).

As may be realized, the body 1020 to which the gripping members 411A, 411B are attached, the grip tube 1010, the transmission member 700 and/or the ejector member 415 described herein (or any other suitable portion of the gripper 111, 111A, 111B that may contact the sample container 150) may be constructed of a low heat conductivity material. In this aspect the low heat conductivity material may allow for connection of the gripping members 411A, 411B, the grip tube 1010, the transmission member 700 and/or the ejector member 415 to respective portions of the drive unit 113 to enable picking and placing of, for example, cryogenic samples within the sample containers 150 while preserving a higher temperature for the moving parts of the drive unit 113.

Figure 12:
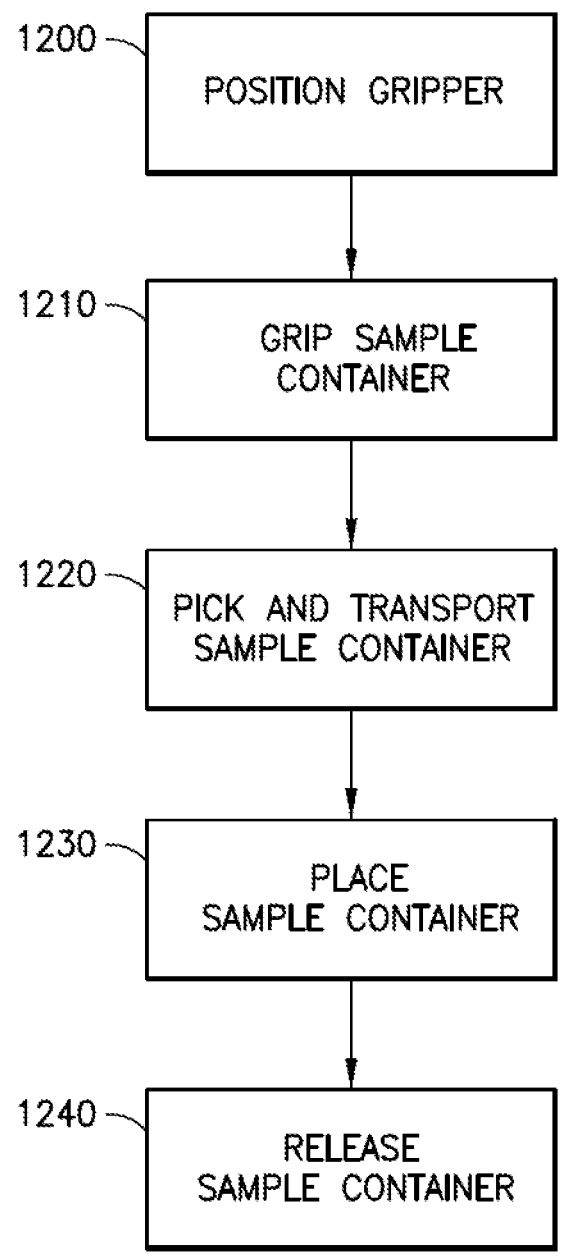
FIG. 12 is a flow diagram in accordance with aspects of the disclosed embodiment.

Referring again to FIG. 10A and also to FIGS. 10B-10H and 12 a picking/placing operation of the gripper 111B will be described. This picking/placing operation may apply to the other grippers described herein however, the direction in which the gripper members move (e.g. towards each other or away from each other—e.g. see FIGS. 2A-2C) for gripping the cap/sample container may change as described herein. The controller 170 may position, using the drive unit 113, the gripper 111B above a predetermined sample container 150 disposed within, for example, a sample tray 140 or any other suitable sample container holding area (FIG. 12, Block 1200) in a manner substantially similar to that described above. The gripping members may be extended or otherwise moved in the direction of arrow 498A so that the gripping members 411B are positioned around or are otherwise aligned with protrusion 900 as shown in FIG. 10B. The gripping members 411B may be moved in the direction of arrow 499 towards the longitudinal axis CX1 of the gripper 111B so that the gripping members 411B engage the protrusion 900 to grip the sample container 150 as shown in FIG. 10C (FIG. 12, Block 1200). As may be realized the gripping of the protrusion 900 with the gripping members 411B may at least in part center or otherwise align the longitudinal axis of the sample container 150 with the longitudinal axis CX1 of the gripper 111B. As may also be realized, the retention features 911R of the gripping members 411B mechanically engage the retention features 900R of the protrusion 900 for positively gripping the sample container 150 in a manner similar to that described above. The drive unit 113 may move the gripping members 411B (and the grip tube and/or ejector member—collectively referred to as the grip head 411BH) in the direction of arrow 498B so that the sample container is moved out of the respective sample container holding area 200 for transport of the sample container 150 (FIG. 12, Block 1220). In one aspect the sample container 150 may be moved into the sleeve 111S, 111S' in any suitable manner. For example, the drive unit 113 may provide sufficient movement of the grip head 411BH holding the sample container 150 in the direction of arrow 498B relative to the sleeve 111S, 111S' to lift the sample container 150 into the sleeve from the sample tray 140. In another aspect, the gripper 111B may be moved in the direction of arrow 498B away from the sample tray and the sleeve 111S, 111S' may be moved in the direction of arrow 498A relative to the grip head 411BH so that the sleeve 111S, 111S' is positioned around the sample container 150 in a manner substantially similar to that described above. In other aspects the grip head 411BH and the sleeve 111S, 111S' may be moved relative to each other in the manner described above for moving the sample container 150 into the sleeve 111S, 111S'. In one aspect the sleeve 111S, 111S' may be moved in the direction of arrow 498A so as to be in close proximity to the sample container 150 to substantially prevent or minimize convective heat exchange from the sample container 150 with an atmosphere surrounding the sample container 150 and/or radiation exposure. The gap G2 between the sleeve 111S, 111S' and the cap and/or sample container may be independent of a position of the grip head 411BH relative to the cap and/or sample container. As the sample container 150 is moved in the direction of arrow 498B into the sleeve the sample container interface members 800 are spread apart in the direction of arrow 499 through contact with the sample container 150. For example, the sample container interface members 800 may include ramp surfaces 800R that interface with the sample container 150 and allow the sample container to pass between the sample container interface members 800 against the biasing force provided by the resilient members 1000. The biasing force provided by the biasing members 1000 is transferred to the sample container 150 through the sample container interface members 800 when the sample container 150 is disposed between the sample container interface members 800 and effects a self-centering of the sample container 150 within the gripper 111B as shown in FIG. 10E. After transport, the sample container 150 may be aligned with (in a manner substantially similar to that described above when picking the sample container) and placed into a sample container holding area 200, in, for example, sample tray 140 or any other suitable sample holding area, by moving the grip head 411BH in the direction of arrow 498A (FIG. 12, Block 1230). As may be realized, one or more of the sample container 150 and the tray 140 may include guide surfaces GS1, GS2 (FIG. 10D) that may guide the sample container 150 into the sample holding area 200. The gripping members 411B may be moved in the direction of arrow 498A so that the gripping members 411B are spread apart releasing the protrusion 900 (and hence the sample container 150) from the gripper 111B (FIG. 12, Block 1240). The gripping members 411B (and the grip head 411BH) may be moved in the direction of arrow 498B to lift the gripping members away from the sample container 150 and sample tray 140. In one aspect the ejector member 415 may be remain in substantial contact (e.g. touching or adjacent) with the protrusion 900 so that as the gripping members 411B are moved in the direction of arrow 498B the sample container remains within the sample holding area 200 in the event the gripping member 411B touch or otherwise drag on the protrusion 900.

Figure 13:
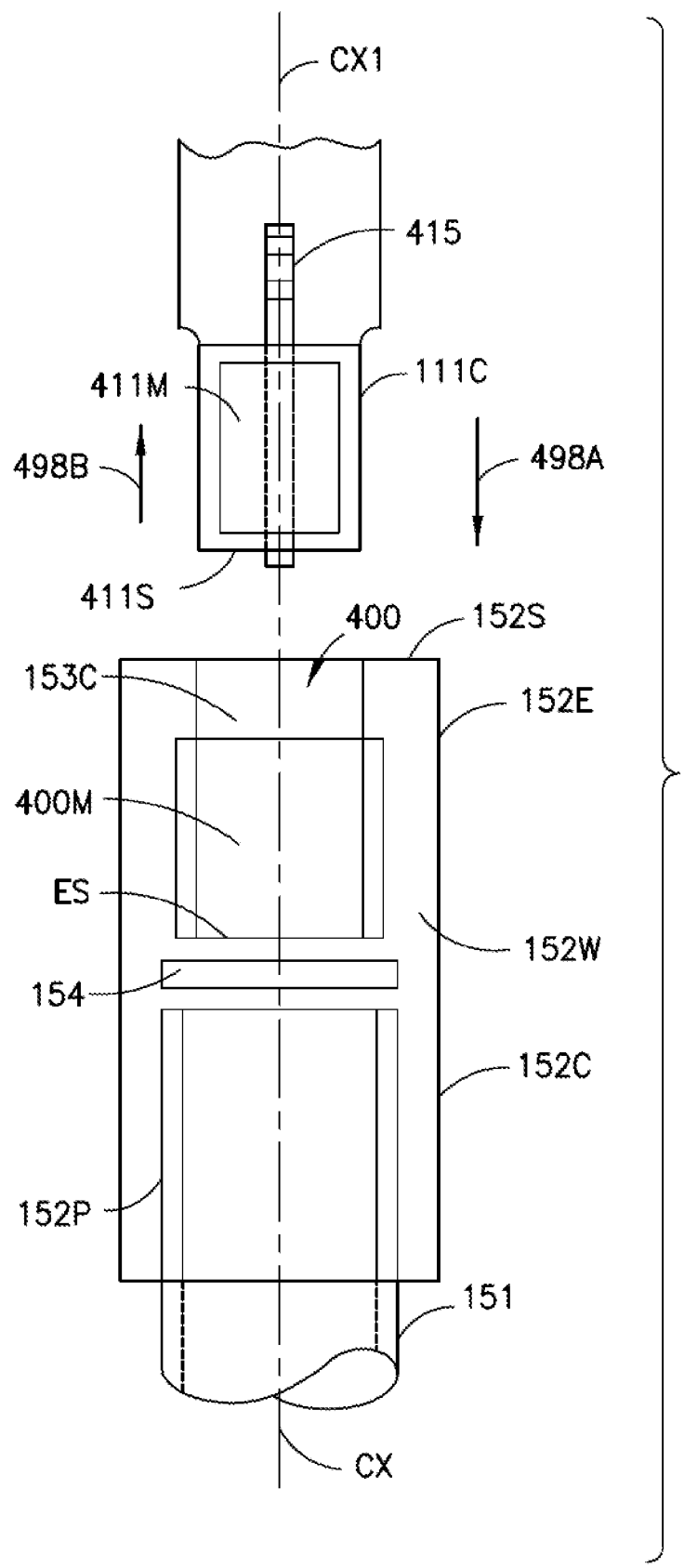
FIG. 13 is a schematic illustration of a portion of the sample storage and retrieval system in accordance with aspects of the disclosed embodiment.

Referring now to FIG. 13, in one aspect the gripper 111C and the transport gripper interface 153C may be configured to magnetically interact with one another and reduce the number of moving parts in the gripper 111C. For example, the cap 152C may be substantially similar to cap 152, 152A described above, however in this aspect the transport gripper interface 153C is configured to magnetically interact with the gripper 111C. For example, the transport gripper interface 153C may include a magnetic gripping member 400M which may be any suitable ferrous material such as a permanent magnet that forms at least a portion of the internal side wall of the cavity 400 and/or is disposed at least partly within the peripheral wall 152W. The gripper 111C, which may be substantially similar to gripper 111, 111A, 111B described above, may include (e.g. instead of gripping members 411A, 411B) a magnetic gripping member 411M that is shaped and sized so that the magnetic gripping member 411M fits at least partly within the cavity 400 (see FIGS. 14A and 14B).

In one aspect the magnetic gripping member 411M may be a permanent magnet that magnetically couples with the magnetic gripping member 400M for magnetically gripping the sample container 150. Here the ejector member 415 may be employed to push against the ejection surface ES to disengage the magnetic gripping members 400M, 411M from each other during placement of the sample container 150. In another aspect the magnetic gripping member 411M may be an electromagnet having one or more electromagnetic coils or electrical windings which may be under the control of controller 170M or any other suitable controller. Here the magnetic gripping member 411M, when activated, may generate an electromagnetic field that produces a motive force in the direction of arrow 498B which may cause, through interaction with the magnetic gripping member 400M, the sample container 150 to move in the direction of arrow 498B towards the gripper 111C until, for example, the ejection surface ES contacts the ejection member 415 and/or a surface 411S (such as a bottom surface) of the gripper 111C. In one aspect the ejection member 415 may not be provided as sufficient clearance may be provided between the gripper 111C and the cavity 400 so that when the magnetic gripping member 411M is turned off or deactivated (or is a direction of the magnetic field is reversed so that the motive force provided by the gripping member 400M is in the direction of arrow 498A as described below) the gripper 111C is freely movable relative to the cavity for releasing the sample container 150 from the gripper 111C. In other aspects the ejection member 415 may not be provided as the magnetic gripping member 411M may be configured to produce, when energized with differing polarities, magnetic forces in the direction of arrow 498B as well as forces in the direction of arrow 498A. For example, when picking a sample container 150 the magnetic gripping member 411M may be activated to produce magnetic gripping forces in the direction of arrow 498B for gripping and lifting the sample container from a respective sample holding area 200. When placing a sample container 150 the magnetic gripping member 411M may be activated to produce magnetic gripping forces in the direction of arrow 498A for releasing and lowering the sample container to a respective sample holding area 200. As may be realized, in one aspect, the magnetic gripping member 411M may be controlled by, for example the controller 170 so that a rate of movement of the sample container caused by the electromagnetic forces of the magnetic gripping member 411M can be controlled in any suitable manner.

Referring to FIGS. 13, 14A and 14B the operation of gripper 111C may be substantially similar to the operation of gripper 111A described above. For example, the controller 170 may position, using the drive unit 113, the gripper 111C above a predetermined sample container 150 disposed within, for example, a sample tray 140 or any other suitable sample container holding area (FIG. 6, Block 600). In one aspect the controller 170 may identify the predetermined sample container 150 in a manner substantially similar to that described above. The gripper 111C is moved in the direction of arrow 498A to position the magnetic gripping member 411M within the cavity 400 (FIG. 6, Block 610). The magnetic gripping member 411M of the gripper 111C magnetically interacts with the magnetic gripping member 400M of the cap 152C for gripping the sample container (FIG. 6, Block 620). As described above, in one aspect the gripping may be a passive gripping such as when magnetic gripping member 411M is a permanent magnet or an active gripping such as when the magnetic gripping member is an electromagnet. The magnetic gripping members 400M, 411M may be arranged so that attractive magnetic forces between the magnetic gripping members 400M, 411M provide self-centering forces for aligning the longitudinal axis CX of the sample container 150 with the longitudinal axis CX1 of the gripper 111C. In one aspect the sample container interface members 800 may be provided in the manner shown in FIG. 10A-10D to further center and stabilize the sample container within the channel 1500. Once the sample container 150 is gripped by the gripper 111C the controller may cause, using the drive unit 113, the sample 150 to be picked from the sample container holding area and transferred from/to the sample tray 140 or from/to any other suitable sample container holding area in a manner substantially similar to that described above (e.g. moving the gripper 111C so that the sample container 150 is disposed within the insulated sleeve 111S—FIG. 6, Block 630). The sample container may be positioned over a predetermined sample holding location, such as a sample container holding area 200 and placed into the holding area (FIG. 6, Block 640). The gripper 111C may release the sample container 150 (FIG. 6, Block 650) and be removed from the cavity 400 (FIG. 6, Block 660). For example, where the gripping is a passive gripping, the drive unit 113 may effect relative movement of the ejector member 415 and the magnetic gripping member 411M so that the ejector member 415 is moved in the direction of arrow 498A against the ejection surface ES while the magnetic gripping member 411M is moved in the direction of arrow 498B to remove the magnetic gripping member 411M from the cavity 400 and release the sample container form the gripper 111C. In other aspects the ejector member 415 may be held stationary against the ejection surface ES (when the sample container is within the holding area 200) while the magnetic gripping member 411M is moved in the direction of arrow 498B out of the cavity 400 to release the sample container 150 from the gripper 111C. In other aspects, where the gripping is an active gripping, the electromagnet may be turned off or the electromagnetic field may be reversed as described above to release the sample container 150 from the gripper 111C.

Referring now to FIGS. 15A and 15B, in one aspect the cap 152D (which may be substantially similar to the caps described above) and the gripper 111D (which may be substantially similar to the grippers described above) may be configured such that the gripper 111D magnetically interacts with a transport gripper interface 153D of the sample container over the cap 152D in a manner similar to that described above with respect to FIGS. 9-12. However, in this aspect gripper 111D may not move in the Z-direction (e.g. in the direction of arrow 498). Here the cap 152D may be substantially similar to cap 152C and transport gripper interface 153D may include magnetic gripping member 400M however, the cavity 400 need not be provided in the cap 152D. The frame 111F of the gripper 111D may include a magnetic gripping member 411M' that is shaped and sized to form a channel 1500 (substantially similar to that shown in FIGS. 10A-11D and 14A-14B and described above) into which a sample container 150 is at least partially inserted.

The magnetic gripping member 411M' may be substantially similar to magnetic gripping member 411M and may include one or more electromagnetic coils or electrical windings which may be under the control of controller 170M or any other suitable controller. Here the magnetic gripping member 411M', when activated, may generate an electromagnetic field that produces a motive force in the direction of arrow 498B which may cause, through interaction with the magnetic gripping member 400M, the sample container 150 to move out of the sample holding area 200 in the direction of arrow 498B (e.g. lift the sample container from the tray or other holding area) towards the gripper 111D until, for example, the sample container 150D is disposed at least partly within the channel 1500 of the gripper 111D as shown in FIG. 15B. The position of the sample container 150 within the gripper 111D may be determined in any suitable manner such as by a configuration of the magnetic field produced by the magnetic gripping member 411M'. The magnetic gripping member 411M' may be configured to produce, when energized with differing polarities, magnetic forces in the direction of arrow 498B as well as forces in the direction of arrow 498A. For example, when picking a sample container 150 the magnetic gripping member 411M' may be activated to produce magnetic gripping forces in the direction of arrow 498B for gripping and lifting the sample container from a respective sample holding area 200. When placing a sample container 150 the magnetic gripping member 411M' may be activated to produce magnetic gripping forces in the direction of arrow 498A for releasing and lowering the sample container to a respective sample holding area 200. As may be realized, in one aspect, the magnetic gripping member 411M' may be controlled by, for example the controller 170 so that a rate of movement of the sample container caused by the electromagnetic forces of the magnetic gripping member 411M' can be controlled in any suitable manner. In one aspect the magnetic gripping member 411M' may include a common electromagnetic coil/winding configured to provide both the lifting (e.g. for moving the sample container in the direction of arrow 498) and gripping forces (e.g. for holding the sample container within the gripper 111D). In other aspects the magnetic gripping member 411M' may include separate (e.g. different) electromagnetic coils/winding sets where at least one coil/winding set is configured to provide the lifting forces and at least another coil/winding set is configured to provide the gripping forces.

Figure 16:
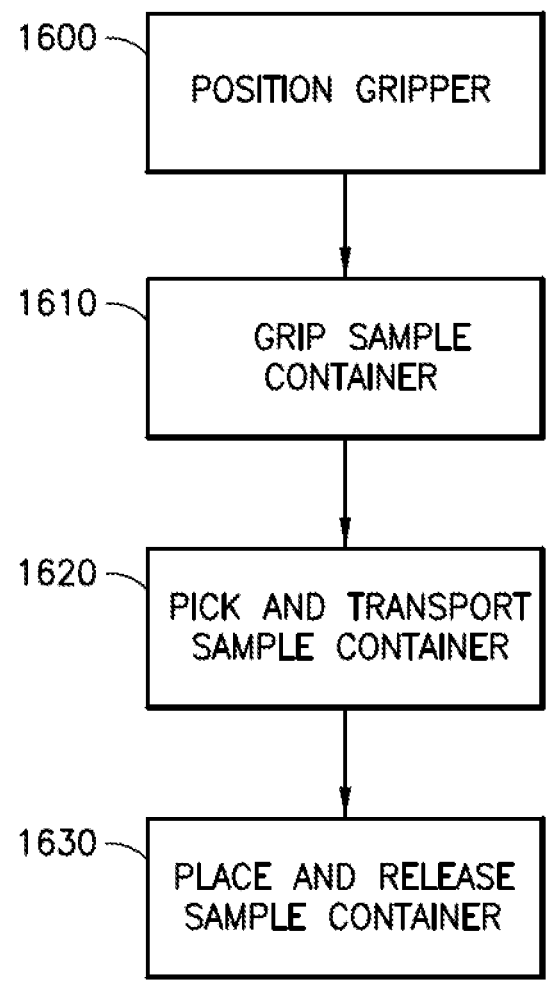
FIG. 16 is a flow diagram in accordance with aspects of the disclosed embodiment.

Referring also to FIG. 16, the operation of the gripper 111D may be substantially similar to that described above with respect to gripper 111B however, there is no Z-axis movement of the gripper 111B. For example, the gripper 111D may be positioned above a predetermined sample container 150 in a manner substantially similar to that described above (FIG. 16, Block 1600). The sample container 150 may be lifted from the respective sample holding area 200 through the magnetic motive forces generated by the magnetic gripping member 411M' as described above so that the sample container is lifted into the gripper and gripped by the magnetic gripping member 411M' (FIG. 16, Block 1610). As may be realized, the magnetic field generated by the magnetic gripping member 411M' may provide self-centering of the sample container 150 within the gripper 111D so that the longitudinal axis CX of the sample container is substantially aligned with the longitudinal axis of the gripper CX1. In one aspect the sample container interface members 800 may be provided in the manner shown in FIG. 10A-10D to further center and stabilize the sample container within the channel 1500. The sample container 150 may be transported to any suitable holding area as described above (FIG. 16, Block 1620). The sample container 150 may be lowered into the sample holding area 200 and released by the gripper in the manner described above, where the magnetic field generated by the magnetic gripping member 411M' lowers the sample container from the gripper 111D and into the sample holding area 200 (FIG. 16, 1630).

Referring now to FIGS. 17, 18, 19 and 20 the transport gripper interface 153A, 153B, 153C, 153D may be included in a module 1700, 1701, 1702, 1703 that is coupled to the cap 152 in any suitable manner. In one aspect the module 1700, 1701, 1702, 1703 may be mechanically fixed, chemically fixed or otherwise be affixed to or fit over the cap 152 in any suitable manner. In one aspect, as shown in FIGS. 17-20 the modules 1700, 1701, 1702, 1703 may snap onto the cap such that the modules 1700, 1701, 1702, 1703 and the cap 152 are movable as a unit. As may be realized, one or more of the identification module 154 and the indicia 155 may be included on or within the modules 1700, 1701, 1702, 1703 in any suitable manner, such as described above. Each of the modules 1700, 1701, 1702, 1703 may be shaped and sized so as to fit within the bounds of the sample holding area 200 of the sample tray 140 as described above with respect to FIGS. 2A and 2B to allow for the "closely packed" array of sample containers 150.

Figure 22:
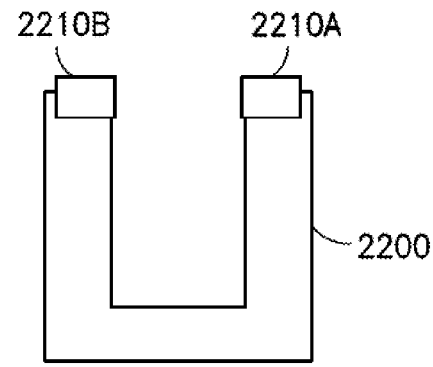
FIG. 22 is a portion of a cap exchange unit in accordance with aspects of the disclosed embodiment.
Figure 23A:
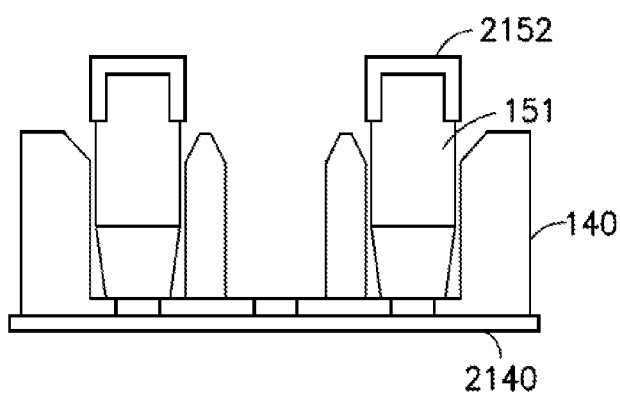
FIGS. 23A-23D are schematic illustrations of a cap exchange in accordance with aspects of the disclosed embodiment.
Figure 23B:
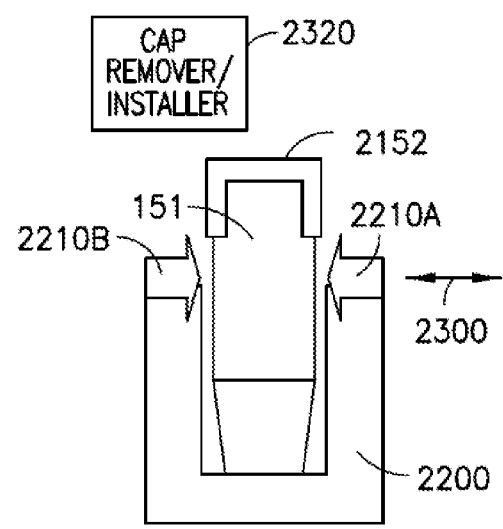
Figure 23C:
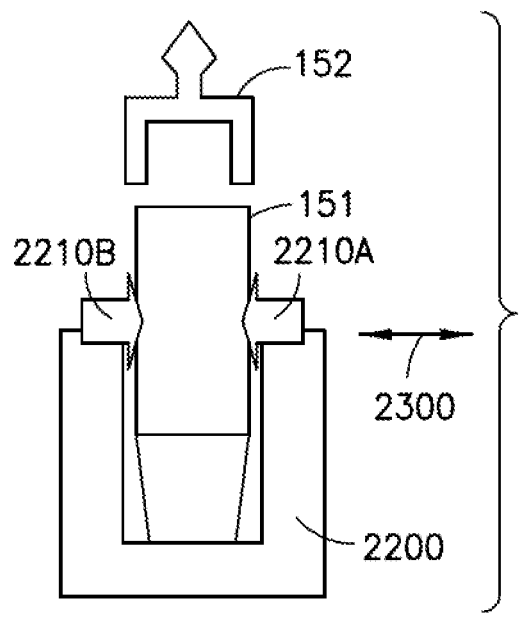
Figure 23D:
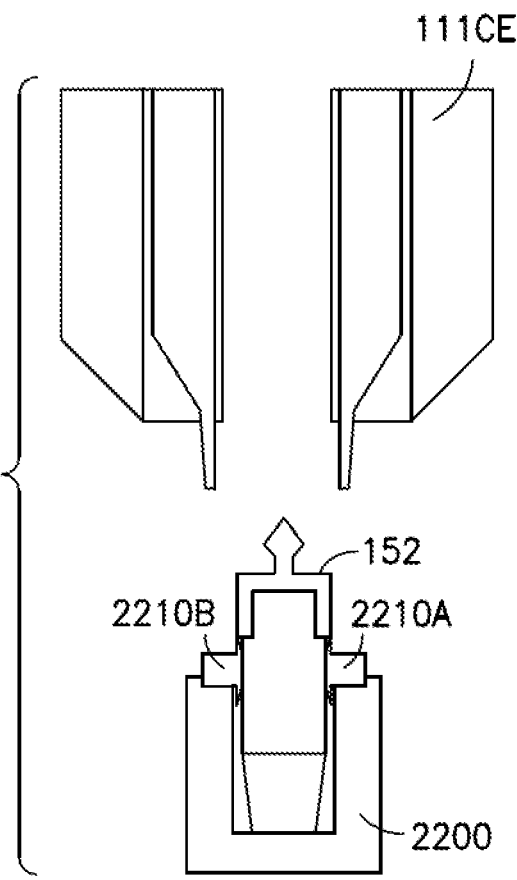
Figure 24:
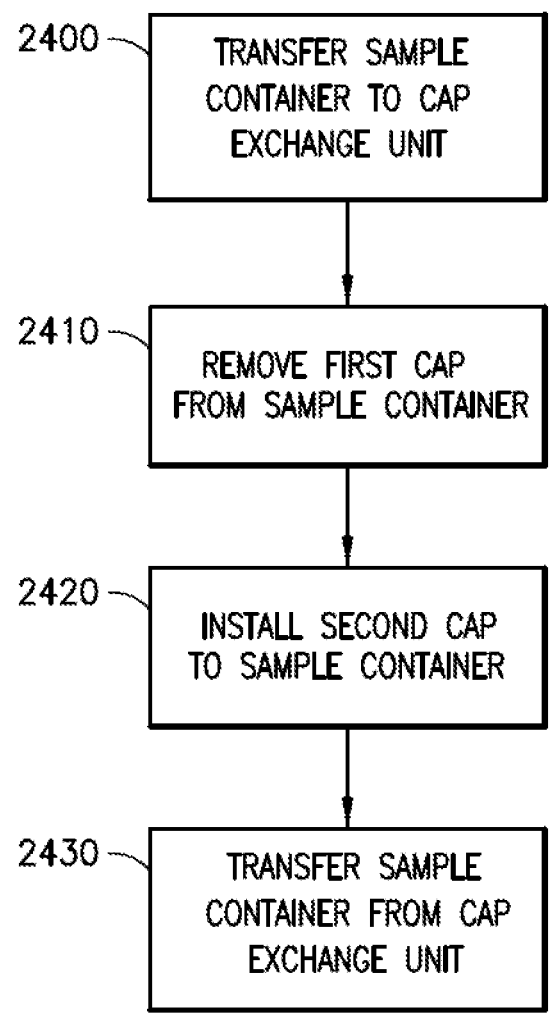
FIG. 24 is a flow diagram in accordance with aspects of the disclosed embodiment.

Referring now to FIGS. 21 and 22, as noted above, the storage and retrieval system 100 may include a cap exchange unit 130C. The cap exchange unit 130C may include a sample container gripper 1110E, at least one sample storage tray holder 2140 and an insulated/refrigerated sample container holder 2200. The sample container gripper 1110E may be substantially similar to grippers 111A, 111B described above. The gripper members 411 of the gripper 1110E are illustrated generally but may be similar to gripper members 411A, 411B so as to grip the caps 152 (described herein) and/or a side of the cap 2152 and/or a side of the sample container 151. The sample storage tray holder 2140 may be configured to hold any suitable number of sample trays 140". The sample container holder 2200 may include any suitable insulation or refrigerant so as to maintain a sample with a sample container 150 held therein at, for example, cold and/or ultra-cold temperatures such as, for exemplary purposes only, temperatures less than about −134° C. As may be realized, the cap exchange unit 130C may retrofit sample containers 150 having conventional caps 2152 with the caps 152 described herein. The sample containers 150 may be holding samples that are already at, for example, ultra-cold temperatures during the retrofitting of the caps 152. For example, referring also to FIGS. 23A-23D and 24, a sample within a sample container 150 may be transferred to the cap exchange unit 130C in any suitable manner (FIG. 24, Block 2400). In one aspect, the sample may be transferred to the cap exchange unit 150 in a sample tray 140" where the sample tray is placed on the holder 2140. Any suitable conveying device, such as a robotic transport, of the storage and retrieval system 100 may transfer the sample tray 140" from a location within the storage area 120 to the cap exchange unit 130C. The gripper 1110E may remove the sample container 150 holding the sample from the sample tray and transfer the sample container 150 to the sample container holder 2200. As noted above, the grip head 411 and the sleeve 111S, 111S' may be moved relative to each other in the manner described above for moving the sample container 150 into the sleeve 111S, 111S'. In one aspect the sleeve 111S, 111S' may be moved in the direction of arrow 498A so as to be in close proximity to the sample container 150 to substantially prevent or minimize convective heat exchange from the sample container 150 with an atmosphere surrounding the sample container 150 and/or radiation exposure.

The sample container holder 2200 may include one or more grippers 2210A, 2210B that move in the direction of arrow 2300 for gripping the sample holder 151 within the sample container holder 2200 so that the cap 2152 (e.g. a first cap) can be removed from the sample holder 151 (FIG. 24, Block 2410). In one aspect the cap exchange unit 130C may include a cap remover/installer 2320 that removes the cap 2152 from the sample holder 151 by, for example, unscrewing the cap, pulling the cap off or removing the cap in any other suitable way. In other aspects the gripper 1110E may be configured to remove the cap by unscrewing the cap, pulling the cap off or removing the cap in any other suitable way. A second cap (e.g. having different characteristics than the first cap), such as one of the caps 152 described above, may be transferred to the sample holder 151 by the cap remover/installer 2320, or in other aspects by the gripper 1110E, and installed on the sample holder in any suitable manner, such as by threading the cap on or by pushing the cap on (FIG. 24, Block 2420). The sample container 150 with the retrofitted cap 152 may be transferred to, for example, a destination sample tray such as those described above with respect to FIGS. 2A and 2B or to any other suitable sample tray such as described above with respect to FIG. 2C (FIG. 24, Block 2430). For example, the grippers 2210A, 2210B may move in the direction of arrow 2300 to release the sample holder 151. The gripper 1110E may pick the sample container 150 from the holder 2200 as described above where the sleeve 111S, 111S' of the gripper insulates the sample within the sample container 150 during transport as described above and the gripping members 411 interface with one or more of the transport gripper interface 153 of caps 152 (as described herein) and/or a side of the cap 2152 and/or a side of the sample container 151. In other aspects the sample container 150 may be returned to the tray 140" (e.g. the tray from which the sample was taken). The sample tray holding retrofitted sample container 150 may be returned to storage or to any other suitable location of the storage and retrieval system.

Figure 26:
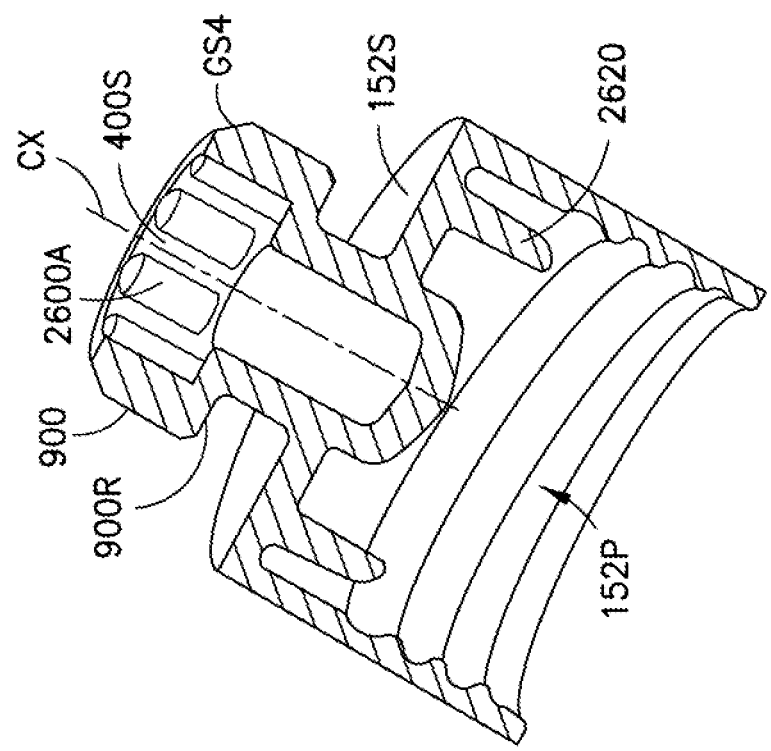
FIG. 26 is a schematic illustration of a sample container cap in accordance with aspects of the disclosed embodiment.
Figure 25:
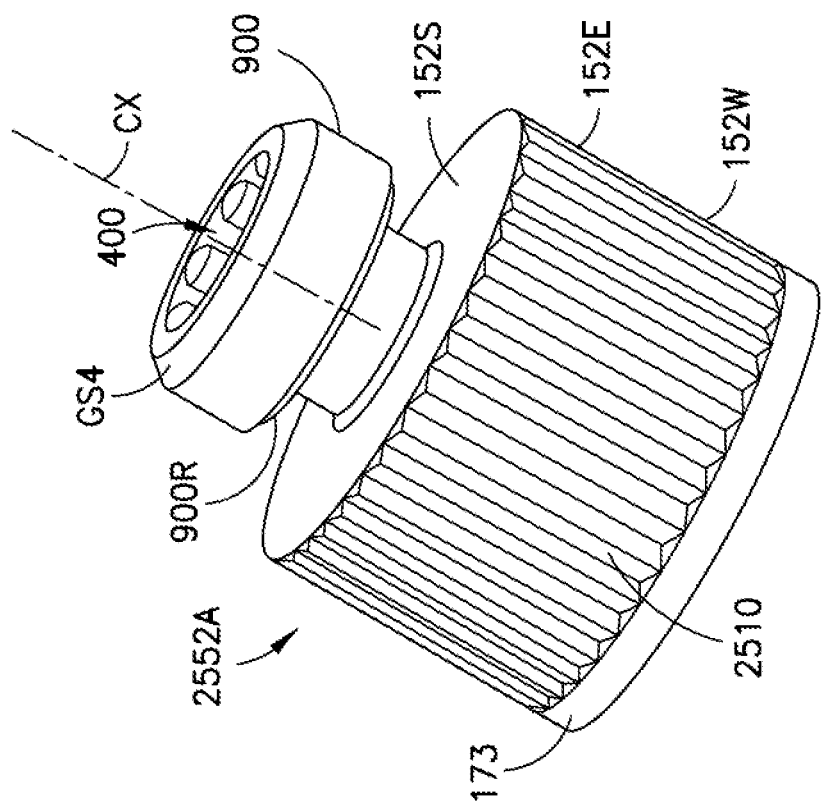
FIG. 25 is a schematic illustration of a sample container cap in accordance with aspects of the disclosed embodiment.
Figure 27:
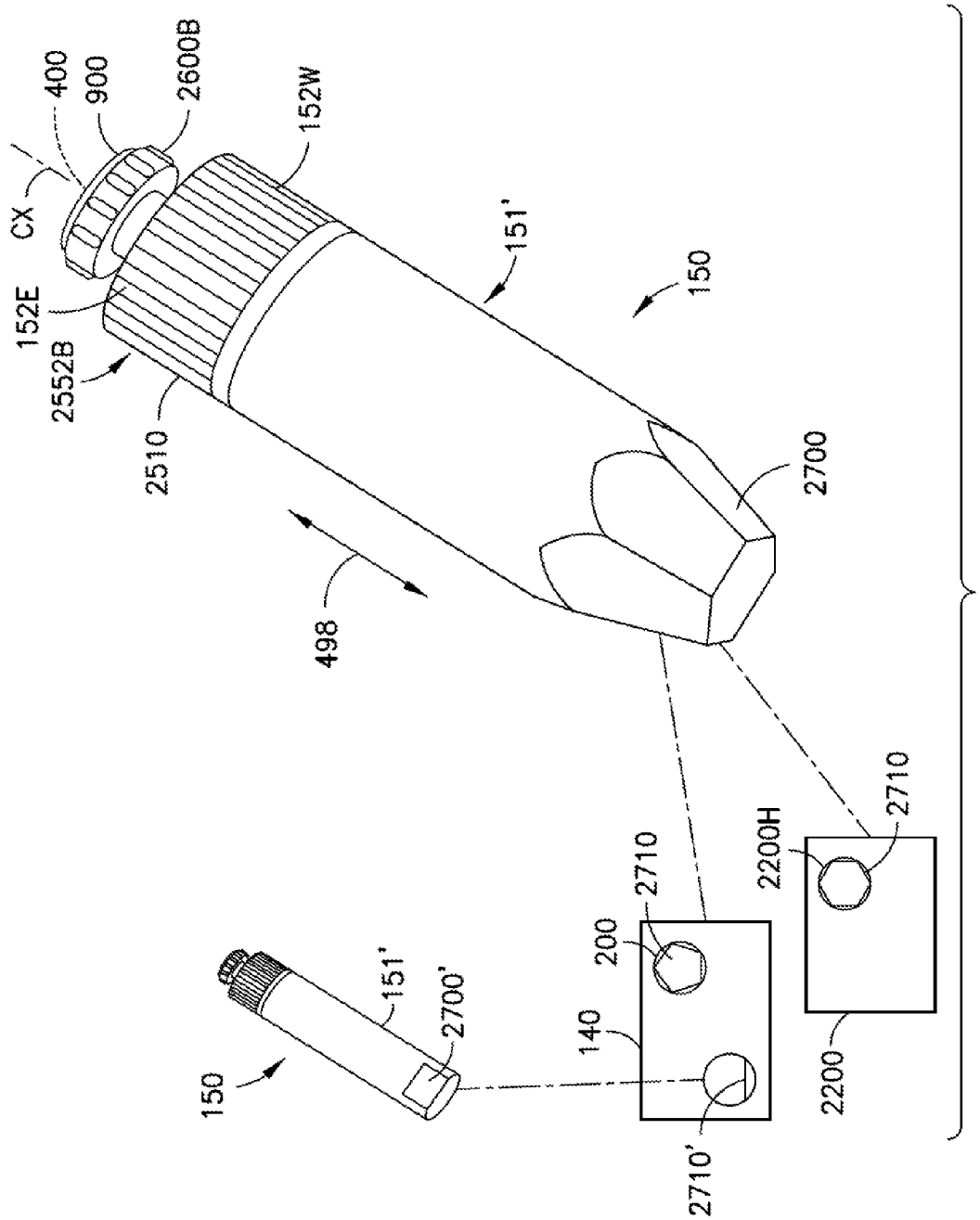
FIG. 27 is a schematic illustration of a sample container in accordance with aspects of the disclosed embodiment.

Referring to FIGS. 25-27 in one aspect of the disclosed embodiment the cap 2552A, 2552B is substantially similar to one or more (e.g. a combination of) caps 152, 152', 152A-152D and 2152 described above. For example, referring to FIGS. 25 and 27 each cap 2552A, 2552B may have a cylindrical body 173 having at least one peripheral wall 152W forming an outer peripheral edge or side 152E of the cap 152 and defining the bounds within which the cap 2552A, 2552B (and hence the sample container 150) is gripped. In one aspect, the side 152E includes any suitable texture such as ridges, knurling, etc. that provides for human gripping of cap 2552A, 2552B and/or the sample container 150 and for removal of the cap 2552A, 2552B from the sample holder 151'. In other aspects the body 173 may have any suitable shape and or configuration. In one aspect, the cap 2552A, 2552B includes an annular sealing member 2620 that extends from the surface 152S so as to be concentric with the at least one peripheral wall 152W so that when the cap is engaged with the sample holder 151' the sample holder is disposed between the at least one peripheral wall 152W and the annular sealing member 2620 (e.g. the outer peripheral wall 152W engages an outside surface of the sample holder 151' while the annular sealing member 2620 engages an inner surface of the sample holder 151'. The annular sealing member 2620 is, in one aspect, made of the same material as the cap 2552A, 2552B (e.g. as a unitary one piece member) while in other aspects the annular sealing member is constructed of any suitable material and has any suitable configuration for forming a seal between the cap 2552A, 2552B and the sample holder 151'.

The cap 2552A, 2552B may include a sample holder engagement portion 152P configured to interface with the cap engagement portion 151P of the sample holder 151' (see FIGS. 1A and 1B) for securing the cap 2552A, 2552B to the sample holder 151'. As noted above, in one aspect the sample holder engagement portion 152P may interface with the cap engagement portion 151P in any suitable manner such that the cap 2552A, 2552B is retained on the sample holder 151 through a frictional engagement, a threaded engagement (e.g., male or female threading—see FIG. 26), a snap engagement, a magnetic engagement or in any other suitable manner. In a manner similar to that described above the cap 2552A, 2552B includes a protrusion 900 that extends from surface 152S of the cap 2552A, 2552B where the protrusion includes one or more retention features 900R configured to positively interface with the grippers described herein, such as for example, gripper 111B.

In this aspect, the protrusion 900 also includes a cavity 400 substantially similar to that described herein where the protrusion provides for the gripping and transport of the sample container 150 and the cavity 400 provides for the removal of the cap 2552A, 2552B from the sample holder 151'. Here the cavity is configured to engage the grippers described herein such as, for example, grippers 111A, 111C, 1110E and/or the cap remover/installer 2320 of the cap exchange unit 130C. In one aspect, as illustrated in FIGS. 25 and 26 the cavity 400 includes a peripheral wall or surface 400S on which one or more grip members 2600A are located. In one aspect the one or more grip members 2600A protrude from surface 400S towards a centerline CX of the cap 2552A. In other aspects the grip members 2600A have any suitable configuration that allows the cap 2552A to be gripped by the gripper 111A, 111C, 1110E and/or the cap remover/installer 2320 and removed from or installed on the sample holder 151' through a rotation of the cap 2552A relative to the sample holder 151' (e.g. to unscrew or screw the cap to/from the sample holder 151') and/or through a linear displacement of the cap 2552A relative to the sample holder 151' (e.g. to pull or push the cap 2552A off/on the sample holder 151' in the direction of arrow 498). In one aspect the peripheral wall of the cavity 400 may have any suitable geometric shape (square, triangular, slotted, pentagonal, hexagonal, octagonal, etc.) that provides for at least a rotationally coupled engagement between the cap 2552A and the gripper 111A, 111C, 1110E and/or the cap remover/installer 2320. In other aspects the grip members 2600A include magnets, similar to that described herein with respect to FIGS. 13-14B, where the magnets are arranged relative to the cavity 400 for at least rotationally coupling the cap 2552A with the gripper 111A, 111C, 1110E and/or the cap remover/installer 2320. While the one or more grip members 2600A are illustrated with respect to cap 2552A it should be understood that the grip member 2600A may be included within the cavities 400 of the other caps described herein (e.g. that do not include a protrusion 900) in combination with the retention features (e.g. such as retention features 400R) so that the cavity 400 provides for both transport of the sample container 150 and removal of the cap from the sample holder.

The grip members 2600A are, in one aspect, configured for a passive engagement with the gripper 111A, 111C, 1110E and/or the cap remover/installer 2320. For example, the grip members 2600A are configured to allow insertion of the gripper 111A, 111C, 1110E and/or the cap remover/installer 2320 into the cavity and rotationally engage the gripper 111A, 111C, 1110E and/or the cap remover/installer 2320 substantially without radial or rotational movement of the gripper 111A, 111C, 1110E and/or the cap remover/installer 2320 relative to the grip members 2600A that would otherwise cause an active gripping or engagement of the grip members 2600A. In other aspects, the grip members 2600A are configured for an active engagement with the gripper 111A, 111C, 1110E and/or the cap remover/installer 2320 such that when inserted into the cavity, the gripper 111A, 111C, 1110E and/or the cap remover/installer 2320 moves radially outward to actively engage the grip members 2600A in a manner substantially similar to that described herein with respect to engagement of the retention features 400R. In other aspects the grip members 2600A are configured for active engagement with the gripper 111A, 111C, 1110E and/or the cap remover/installer 2320 through at least a partial rotation of the gripper 111A, 111C, 1110E and/or the cap remover/installer 2320 relative to the grip members 2600A.

Referring to FIG. 27, the cap 2552B is substantially similar to cap 2552A however, in this aspect the grip members 2600B are disposed on a peripheral surface of the protrusion 900 so as to extend outward from the centerline CX of the cap 2552B. In this aspect, the grip members 2600B have any suitable configuration that allows the cap 2552B to be gripped by a gripper 111B and/or the cap remover/installer 2320 and removed from or installed on the sample holder 151' through a rotation of the cap 2552B relative to the sample holder 151' (e.g. to unscrew or screw the cap to/from the sample holder 151') and/or through a linear displacement of the cap 2552B relative to the sample holder 151' (e.g. to pull or push the cap 2552B off/on the sample holder 151' in the direction of arrow 498). In one aspect the peripheral wall of the protrusion 900 may have any suitable geometric shape (square, triangular, slotted, pentagonal, hexagonal, octagonal, etc.) that provides for at least a rotationally coupled engagement between the cap 2552B and the gripper 111B and/or the cap remover/installer 2320. In other aspects the grip members 2600B include magnets, similar to that described herein with respect to FIGS. 13-14B (but disposed around the periphery of the external surface of protrusion rather than around a periphery of the internal cavity 400), where the magnets are arranged relative to the protrusion 900 for at least rotationally coupling the cap 2552B with the gripper 111B and/or the cap remover/installer 2320. While the one or more grip members 2600B are illustrated with respect to cap 2552B it should be understood that the grip member 2600B may be included on the protrusion 900 of the other caps described herein (e.g. that do not include cavity 400) in combination with the retention features (e.g. such as retention features 900R as shown in FIG. 27) so that the protrusion provides for both transport of the sample container 150 and removal of the cap from the sample holder.

In a manner similar to that described respect to grip members 2600A, the grip members 2600B are, in one aspect, configured for a passive engagement with the gripper 111B and/or the cap remover/installer 2320. For example, the grip members 2600B are configured to allow passage of the gripper 111B and/or the cap remover/installer 2320 around the periphery of the protrusion and rotationally engage the gripper 111B and/or the cap remover/installer 2320 substantially without radial or rotational movement of the gripper 111B and/or the cap remover/installer 2320 relative to the grip members 2600B that would otherwise cause an active gripping or engagement of the grip members 2600B. In other aspects, the grip members 2600B are configured for an active engagement with the gripper 111B such that when the gripper 111B and/or the cap remover/installer 2320 substantially surrounds the protrusion 900, the gripper 111B and/or the cap remover/installer 2320 moves radially inward to actively engage the grip members 2600B in a manner substantially similar to that described herein with respect to engagement of the retention features 900R. In other aspects the grip members 2600B are configured for active engagement with the gripper 111B and/or the cap remover/installer 2320 through at least a partial rotation of the gripper 111B and/or the cap remover/installer 2320 relative to the grip members 2600B.

Still referring to FIG. 27, the sample holder 151' is substantially similar to sample holder 151 described herein (see FIGS. 1A, 1B) however, in this aspect the closed end of the sample holder 151' includes orientation or anti-rotational features 2700 that engage, for example, corresponding orientation or anti-rotational features 2710 disposed within the holding areas 200 of the sample trays 140 and/or within the holding areas 2200H of the insulated/refrigerated sample container holder 2200 of the cap exchange unit 130C. The anti-rotational features 2710 may have any suitable configuration such as the chamfered/tapered hexagonal shape illustrated in FIG. 27, a ribbed configuration where the ribs radially extend from the sample holder 151' (in a manner similar to grip members 2600B), or any other geometrical shape such as, for example, square, triangular, slotted, pentagonal, hexagonal, octagonal, etc. that provides for at least a rotationally coupled engagement between the sample holder 151' and the sample trays 140 and/or the insulated/refrigerated sample container holder 2200. As noted above, the anti-rotational features 2710 of the sample trays 140 and/or the holding areas 2200H of the insulated/refrigerated sample container holder 2200 have a shape that corresponds with the shape of the anti-rotational feature 2710 of the sample holder 151'. In one aspect, the shape of orientation or anti-rotational features 2700', 2710' is polarized with respect to the sample tray 140 and/or the insulated/refrigerated sample container holder 2200 so that the sample holder 151' is inserted into the sample tray 140 and/or the insulated/refrigerated sample container holder 2200 in a predetermined rotational (about axis CX) orientation relative to the sample tray 140 and/or the insulated/refrigerated sample container holder 2200. In other aspects, the shape of the anti-rotational features 2700, 2710 are not polarized so that the sample holder 151' is inserted in into the sample tray 140 and/or the insulated/refrigerated sample container holder 2200 with any suitable rotational (about axis CX) orientation relative to the sample tray 140 and/or the insulated/refrigerated sample container holder 2200.

Figure 28:
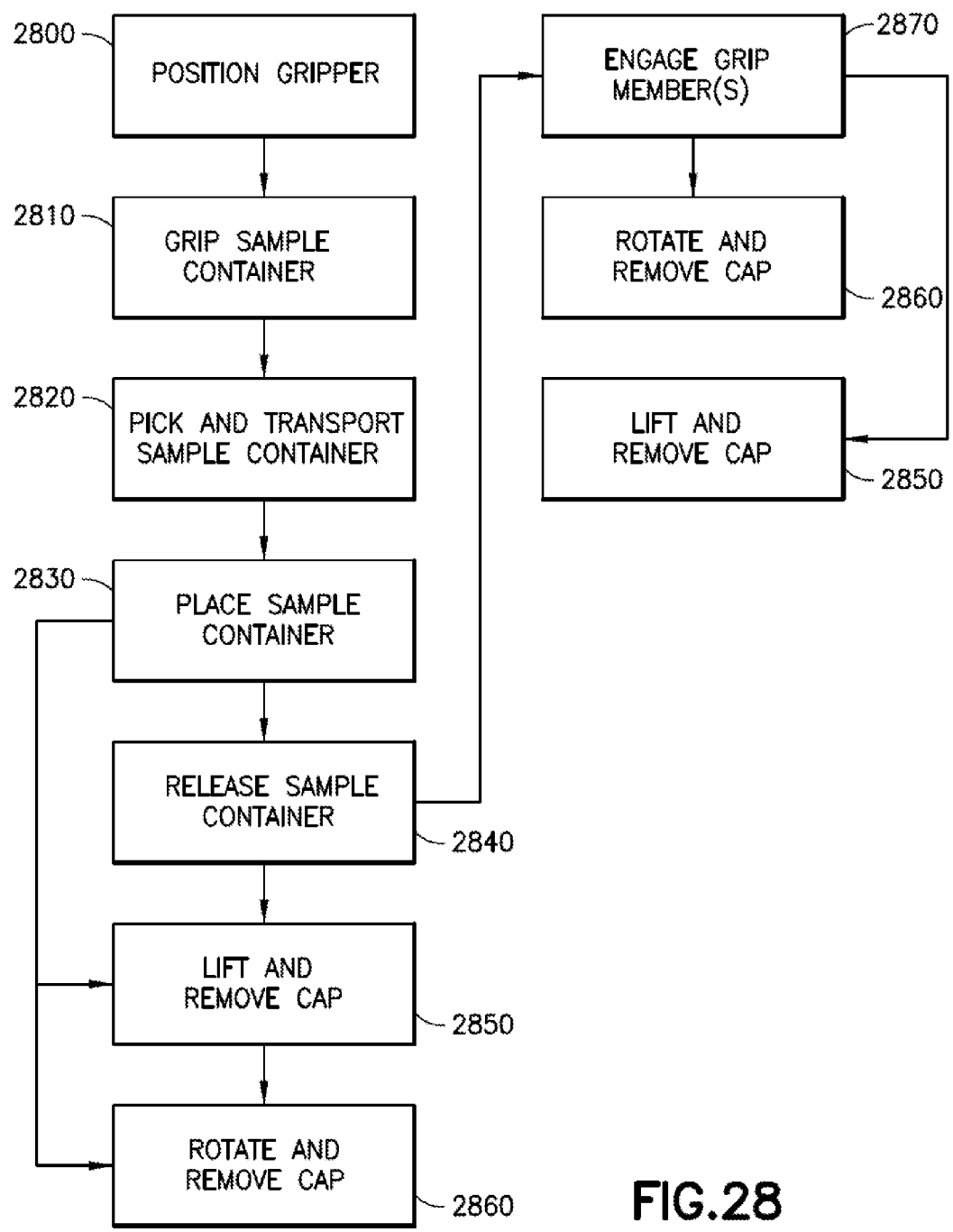
FIG. 28 is a flow diagram in accordance with aspects of the disclosed embodiment.

Referring also to FIG. 28, in one aspect the sample container 150 is transported and cap 2552A, 2552B is removed with a common gripper, substantially similar to grippers 111A, 111B, 111C, 1110E and/or the cap remover/installer 2320. For example, the gripper 111A, 111B, 111C, 1110E and/or the cap remover/installer 2320 is positioned relative to the protrusion 900 and/or cavity 400 in a manner substantially similar to that described herein (FIG. 28, Block 2800). The gripper 111A, 111B, 111C, 1110E and/or the cap remover/installer 2320 is positioned around the protrusion 900 or inserted into the cavity 400 and grips the cap 2552A, 2552B of the sample container 150 (FIG. 28, Block 2810). The sample container 150 is picked and transported to any suitable location as described herein (FIG. 28, Block 2820). The sample container is placed at any desired location (FIG. 28, Block 2830). In one aspect, the cap 2552A, 2552B is removed from the sample holder 151' by lifting/pulling the cap 2552A, 2552B linearly off of the sample holder 151' (e.g. single axis movement along axis CX, in the direction of arrow 498, without substantial rotation of the cap) (FIG. 28, Block 2850). In this aspect the sample holder is retained within a holding area of the sample tray 140 and/or a holding area 2200H of the insulated/refrigerated sample container holder 2200 in any suitable manner such as those described herein. In one aspect, the engagement between the anti-rotational features 2700, 2710, 2700', 2710' is, for example, a frictional or other retained engagement that overcomes any cap removal forces generated when the cap 2552A, 2552B is pulled off of the sample holder 151' (e.g. so that the sample holder 151' is retained within the holding area). In another aspect, the cap 2552A, 2552B is removed from the sample holder 151' by rotating the cap 2552A, 2552B relative to the sample holder 151' (e.g. unscrewing the cap) where the sample holder is held rotationally fixed by the anti-rotational features 2700, 2710, 2700', 2710' (FIG. 28, Block 2860). Where the sample container 150 and the cap 2552A, 2552B are removed by a common gripper the gripper may engage the grip members 2600A, 2600B when the protrusion 900 or cavity 400 is engaged by the gripper.

In another aspect, the sample container 150 is transported and the cap 2552A, 2252B is removed by different grippers. For example, the sample container 150 is transported and placed at a holding area as described herein using one of the protrusion 900 and the cavity 400 (see for example, FIG. 28, Blocks 2800-2830). Here the transport gripper, such as gripper 111A, 111B, 111C, 1110E, releases the cap 2552A, 2552B (FIG. 28, Block 2840) so as to allow another gripper, such the cap remover/installer 2320 or any other suitable gripper, to engage one of grip members 2600A and grip members 2600B (FIG. 28, Block 2870). In one aspect the sample container 150 may be transported by gripping an exterior surface of the protrusion 900 (e.g. through engagement of retention feature 900R) and the cap 2552A, 2552B may be removed by gripping/engaging the grip members 2600A (FIG. 28, Block 2870) disposed within the cavity 400 of the protrusion 900. In another aspect the sample container 150 may be transported by gripping an interior surface of the cavity (e.g. through engagement of retention feature 400R) and the cap 2552A, 2552B may be removed by gripping/engaging the grip members 2600B (FIG. 28, Block 2870) disposed around a periphery of the protrusion 900. The cap 2552A, 2552B is removed from the sample holder 151' in the manner described herein by rotating the cap 2552A, 2552B (FIG. 28, Block 2860) or by lifting/pulling the cap 2552A, 2552B (FIG. 28, Block 2850) from the sample holder 151'. The cap 2552A, 2552B may be installed on the sample holder 151' in a manner that is substantially opposite to that described above.

In accordance with one or more aspects of the disclosed embodiment a sample storage includes a frame; and an array of sample container holding areas disposed within the frame where a spacing between adjacent sample container holding areas is independent of a gripping area for sample containers held by the sample storage.

In accordance with one or more aspects of the disclosed embodiment the sample container holding areas are configured to hold test tubes.

In accordance with one or more aspects of the disclosed embodiment the gripping area for each sample container is substantially within a perimeter of a respective sample container holding area.

In accordance with one or more aspects of the disclosed embodiment the frame and the array of sample container holding areas forms a sample tray.

In accordance with one or more aspects of the disclosed embodiment the sample tray is configured to interact with an automated sample transport system.

In accordance with one or more aspects of the disclosed embodiment the spacing between each sample container holding area allows for closely packed sample containers such that a gap between adjacent sample container walls is non-deterministic for gripper access of the adjacent sample containers.

In accordance with one or more aspects of the disclosed embodiment a sample container includes a sample holder having a central axis, an opening and an internal cavity, in communication with the opening, for holding a sample; and a cap having a sample holder engagement portion configured to close the opening and engage the sample holder, the cap having an outer peripheral edge and a transport gripper interface disposed within bounds of the outer peripheral edge.

In accordance with one or more aspects of the disclosed embodiment the transport gripper interface is configured to mechanically interact with a transport gripper.

In accordance with one or more aspects of the disclosed embodiment the transport gripper interface includes a recess having at least one internal side wall configured to engage a transport gripper such that mechanical forces exerted by the transport gripper on the at least one internal side wall radiate from the central axis.

In accordance with one or more aspects of the disclosed embodiment the cap includes a cap surface disposed opposite the sample holder engagement portion and the transport gripper interface includes a protrusion extending from the cap surface.

In accordance with one or more aspects of the disclosed embodiment the transport gripper interface is configured to magnetically interact with a transport gripper.

In accordance with one or more aspects of the disclosed embodiment the transport gripper interface includes a ferrous material or magnet configured to interface with a magnetic gripper.

In accordance with one or more aspects of the disclosed embodiment the transport gripper interface includes a recess having at least one internal side wall configured so that the transport gripper interface magnetically interfaces with a transport gripper inserted into the recess.

In accordance with one or more aspects of the disclosed embodiment the transport gripper interface includes a cap surface disposed opposite the sample holder engagement portion where the cap surface is configured to magnetically interface with a transport gripper disposed adjacent the cap surface.

In accordance with one or more aspects of the disclosed embodiment the cap further includes a sample identification module.

In accordance with one or more aspects of the disclosed embodiment the sample identification portion is disposed within the cap.

In accordance with one or more aspects of the disclosed embodiment the transport gripper interface and the sample identification module are arranged relative to one another so that the sample identification module is readable when one or more of a gripper passes over the sample container, and a gripper engages the transport gripper interface.

In accordance with one or more aspects of the disclosed embodiment the sample identification module is a radio frequency identification module.

In accordance with one or more aspects of the disclosed embodiment the sample container further includes one or more of a bar code and data matrix configured for optical or fluorescent sample identification readouts.

In accordance with one or more aspects of the disclosed embodiment the sample container further includes an identification module into which the sample holder is placed where the one or more of a bar code and data matrix is disposed on a surface of the identification module.

In accordance with one or more aspects of the disclosed embodiment the transport gripper interface includes a coupling configured to couple the transport gripper interface to the cap.

In accordance with one or more aspects of the disclosed embodiment the transport gripper interface includes one or more of a bar code and data matrix configured for optical or fluorescent sample identification readouts.

In accordance with one or more aspects of the disclosed embodiment one or more of the sample holder and cap includes one or more of a temperature sensor, an accelerometer, orientation sensors, position sensors, location sensors, a data logging device, a radiation sensor, a light sensor, a shock sensor and a stress sensor, electronic or non-electronic memory devices and electronic or non-electronic indicators of handling history.

In accordance with one or more aspects of the disclosed embodiment, the one or more of the sample holder and cap includes one or more of a temperature sensor, an accelerometer, orientation sensors, position sensors, location sensors, a data logging device, a radiation sensor, a light sensor, a shock sensor and a stress sensor, electronic or non-electronic memory devices and electronic or non-electronic indicators of handling history that are configured to be read by one or more of direct observation and remotely.

In accordance with one or more aspects of the disclosed embodiment a sample storage and retrieval system includes at least one sample container having at least one peripheral wall forming an opening, a cavity in communication with the opening and a cap configured to engage the at least one peripheral wall and close the opening; and a sample transport including a frame, a gripper drive unit connected to the frame, and a sample container gripper connected to the gripper drive unit, the gripper being configured to transport a sample container through engagement with the sample container within the bounds of the at least one peripheral wall.

In accordance with one or more aspects of the disclosed embodiment the sample container gripper is configured to draw the sample container mostly or completely within the sample container gripper.

In accordance with one or more aspects of the disclosed embodiment the cap includes a transport gripper interface and the sample container gripper is configured to mechanically interact with transport gripper interface for gripping the sample container.

In accordance with one or more aspects of the disclosed embodiment the transport gripper interface includes a recess having at least one internal side wall configured to engage the sample container gripper such that mechanical forces exerted by the sample container gripper on the at least one internal side wall radiate from a central axis of the sample container.

In accordance with one or more aspects of the disclosed embodiment the cap includes a cap surface disposed opposite the sample holder engagement portion and the transport gripper interface includes a protrusion extending from the cap surface.

In accordance with one or more aspects of the disclosed embodiment the cap includes a transport gripper interface and the sample container gripper is configured to magnetically interact with transport gripper interface for gripping the sample container.

In accordance with one or more aspects of the disclosed embodiment the transport gripper interface includes a ferrous material or magnet configured to interface with the sample container gripper.

In accordance with one or more aspects of the disclosed embodiment the sample container gripper includes one or more of an electromagnet and electric windings configured to produce a magnetic field.

In accordance with one or more aspects of the disclosed embodiment the one or more of an electromagnet and electric windings effect movement of the sample container for insertion and removal of the sample container from the sample container gripper.

In accordance with one or more aspects of the disclosed embodiment the transport gripper interface includes a recess having at least one internal side wall and the sample container gripper is configured for insertion into the recess to magnetically interface with the transport gripper interface.

In accordance with one or more aspects of the disclosed embodiment the transport gripper interface includes a cap surface disposed opposite the sample holder engagement portion where the cap surface is configured to magnetically interface with the transport gripper disposed adjacent the cap surface.

In accordance with one or more aspects of the disclosed embodiment the cap further includes a sample identification module.

In accordance with one or more aspects of the disclosed embodiment the sample identification module is disposed within the cap.

In accordance with one or more aspects of the disclosed embodiment the cap includes a transport gripper interface, the transport gripper interface and the sample identification module being arranged relative to one another so that the sample identification module is readable when one or more of the sample container gripper passes over the sample container, and the sample container gripper engages the transport gripper interface.

In accordance with one or more aspects of the disclosed embodiment sample storage and retrieval system further includes a sample tray having a sample tray frame; and an array of sample container holding areas disposed within the frame where a spacing between adjacent sample container holding areas is such that a gap between the at least one peripheral wall of adjacent sample containers is non-deterministic for sample container gripper access of each of the adjacent sample containers.

In accordance with one or more aspects of the disclosed embodiment the cap includes a transport gripper interface disposed substantially within a perimeter of a respective sample container holding area.

In accordance with one or more aspects of the disclosed embodiment the sample container gripper is configured to center the at least one sample container within the sample container gripper during gripping of the sample container.

In accordance with one or more aspects of the disclosed embodiment one or more of the sample holder and cap includes one or more of a temperature sensor, an accelerometer, orientation sensors, position sensors, location sensors, a data logging device, a radiation sensor, a light sensor, a shock sensor and a stress sensor, electronic or non-electronic memory devices and electronic or non-electronic indicators of handling history.

In accordance with one or more aspects of the disclosed embodiment, the one or more of the sample holder and cap includes one or more of a temperature sensor, an accelerometer, orientation sensors, position sensors, location sensors, a data logging device, a radiation sensor, a light sensor, a shock sensor and a stress sensor, electronic or non-electronic memory devices and electronic or non-electronic indicators of handling history that are configured to be read by one or more of direct observation and remotely.

In accordance with one or more aspects of the disclosed embodiment the sample transport includes an insulated sleeve where at least one of the insulated sleeve and the sample container gripper are movable relative to the other one of the insulated sleeve and the sample container gripper, the insulated sleeve being configured to substantially prevent convective heat exchange between the sample container carried by the sample transport and an environment surrounding the sample container and sample transport.

In accordance with one or more aspects of the disclosed embodiment a gap between the insulated sleeve and the sample container is independent of a position of the sample container gripper.

In accordance with one or more aspects of the disclosed embodiment a sample container transport system includes a frame; a drive unit connected to the frame; a sample container gripper connected to the frame, the sample container gripper including at least one sample container gripping member having a sample container interface configured for gripping and holding a sample container, and a side insulation member having a channel in which the at least one sample container gripper is disposed; wherein the drive unit is configured to effect relative movement between the at least one sample container gripping member and the side insulation member so that a sample container held by the at least one sample container gripping member is transported within the channel of the side insulation member.

In accordance with one or more aspects of the disclosed embodiment the side insulation member includes at least one refrigerant reservoir configured to maintain a temperature of the sample container.

In accordance with one or more aspects of the disclosed embodiment the relative movement between the at least one sample container gripping member and the side insulation member causes an opening and closing of the at least one sample container gripping member for gripping and releasing the sample container.

In accordance with one or more aspects of the disclosed embodiment the side insulation member includes at least one biasing member configured to interface with the sample container.

In accordance with one or more aspects of the disclosed embodiment the at least one sample container gripping member is configured to interface with the sample container within an area bound by a peripheral wall of the sample container.

In accordance with one or more aspects of the disclosed embodiment a gap between the side insulation member and the sample container is independent of a position of the at least one sample container gripping member.

In accordance with one or more aspects of the disclosed embodiment the sample container gripper is configured to draw the sample container mostly or completely within one or more of the sample container gripper and the side insulation member.

In accordance with one or more aspects of the disclosed embodiment a sample container includes a sample holder; and a cap having a sample holder engagement member configured to engage the sample holder, and a protrusion extending opposite the sample holder engagement member, the protrusion including an exterior peripheral surface having one or more retention features configured to effect transport of the sample container cap, and a cavity having an interior surface where the interior surface includes grip members configured to effect a coupling and a decoupling of the sample container cap to and from the sample holder.

In accordance with one or more aspects of the disclosed embodiment the sample holder engagement member is configured for threaded engagement with the sample holder.

In accordance with one or more aspects of the disclosed embodiment the sample holder engagement member is configured for frictional engagement with the sample holder.

In accordance with one or more aspects of the disclosed embodiment the sample holder engagement member includes an annular seal configured to engage an opening of the sample holder.

In accordance with one or more aspects of the disclosed embodiment the one or more retention features include a detent or groove configured to engage a sample container transport gripper.

In accordance with one or more aspects of the disclosed embodiment the grip members extend from the interior surface towards a centerline of the sample container.

In accordance with one or more aspects of the disclosed embodiment the grip members are configured for passive engagement with a cap gripper.

In accordance with one or more aspects of the disclosed embodiment the grip members are configured for active engagement with a cap gripper.

In accordance with one or more aspects of the disclosed embodiment the sample holder includes an open end and a closed end, the open end being configured to engage the cap and the closed end having anti-rotation features that effect relative rotation between the sample holder and the cap.

In accordance with one or more aspects of the disclosed embodiment the sample holder includes an open end and a closed end, the open end being configured to engage the cap and the closed end having orientation features that engage corresponding orientation features of a sample container holding area effect retention of the sample holder within the sample container holding area and relative movement between the sample holder and the cap.

In accordance with one or more aspects of the disclosed embodiment the sample holder engagement member includes a textured external peripheral surface.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the invention.

What is claimed is:

1. A sample storage and retrieval system comprising:
at least one sample container having at least one peripheral wall forming an opening, a cavity in communication with the opening and a cap configured to engage the at least one peripheral wall and close the opening; and
a sample transport including a frame, a gripper drive unit connected to the frame, and a sample container gripper connected to the gripper drive unit, the gripper being configured to transport a sample container through engagement with the sample container within the bounds of the at least one peripheral wall
wherein the sample transport includes an insulated sleeve connected to the frame so that at least one of the insulated sleeve and the sample container gripper are movable relative to the other one of the insulated sleeve and the sample container gripper, the insulated sleeve being configured to substantially prevent convective heat exchange between the sample container carried by the sample transport and an environment surrounding the sample container and sample transport.

2. The sample storage and retrieval system of claim 1, wherein a gap between the insulated sleeve and the sample container is independent of a position of the sample container gripper.

3. A sample container transport system comprising:
a frame;
a drive unit connected to the frame; and
a sample container gripper connected to the frame, the sample container gripper including at least one sample container gripping member having a sample container interface configured for gripping and holding a sample container, and an insulation member having a channel in which the at least one sample container gripper is disposed;
wherein the drive unit is connected to at least one of the sample container gripper and the insulation member and is configured so as to effect relative movement between the at least one sample container gripping member and the insulation member so that a sample container held by the at least one sample container gripping member is transported within the channel of the insulation member along sides of the sample container.

4. The sample container transport system of claim 3, wherein the side insulation member includes at least one refrigerant reservoir configured to maintain a temperature of the sample container.

5. The sample container transport system of claim 3, wherein the side insulation member includes at least one biasing member configured to interface with the sample container.

6. The sample container transport system of claim 3, wherein the at least one sample container gripping member is configured to interface with the sample container within an area bound by a peripheral wall of the sample container.

7. The sample container transport system of claim 3, wherein the sample container gripper is configured to draw the sample container mostly or completely within one or more of the sample container gripper and the side insulation member.

* * * * *